(12) United States Patent
Woerlee et al.

(10) Patent No.: US 10,720,964 B2
(45) Date of Patent: Jul. 21, 2020

(54) DEVICE FOR WIRELESS TRANSMISSION OF DATA AND/OR POWER

(71) Applicant: KONINKLIJKE PHILIPS N.V., Eindhoven (NL)

(72) Inventors: Pierre Hermanus Woerlee, Valkenswaard (NL); Josephus Arnoldus Henricus Maria Kahlman, Tilburg (NL); Nicolaas Lambert, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/468,116

(22) PCT Filed: Dec. 24, 2017

(86) PCT No.: PCT/EP2017/084572
§ 371 (c)(1),
(2) Date: Jun. 10, 2019

(87) PCT Pub. No.: WO2018/127440
PCT Pub. Date: Jul. 12, 2018

(65) Prior Publication Data
US 2019/0386709 A1 Dec. 19, 2019

(30) Foreign Application Priority Data

Jan. 4, 2017 (EP) .................................. 17150246

(51) Int. Cl.
*H04B 5/00* (2006.01)
*H04B 5/02* (2006.01)
(Continued)

(52) U.S. Cl.
CPC ......... *H04B 5/0037* (2013.01); *H04B 5/0075* (2013.01); *H04B 5/02* (2013.01); *A61B 5/00* (2013.01); *H02J 50/10* (2016.02)

(58) Field of Classification Search
CPC .................................................... H04B 5/0037
See application file for complete search history.

(56) References Cited

U.S. PATENT DOCUMENTS

2002/0140547 A1  10/2002  Litwin, Jr. et al.
2007/0254726 A1  11/2007  Iida
(Continued)

FOREIGN PATENT DOCUMENTS

WO  2015196164 A2  12/2015

OTHER PUBLICATIONS

International Search Report and Written Opinion, International Application No. PCT/EP2017/084572, dated Apr. 5, 2018.
(Continued)

*Primary Examiner* — Daniel J Cavallari

(57) ABSTRACT

The present invention relates to a device (700a, 700b, 700c) for wireless transmission of data and/or power between the device and another device of a system, in particular of a patient monitoring system. To meet stringent relative time errors at low complexity the device comprises a connector (701) comprising a data transmission unit (703) and a magnetic coupling unit (702, 704) for transmitting power to and/or receiving power. A detection unit (705) detects coupling of a counterpart connector of another device of the system with the connector (701). A control unit (707) uses the detection that a counterpart connector of another device of the system has been coupled with the connector (701) as a trigger to determine and/or reset a relative time difference between a clock signal used by the device and a clock signal of the other device using i) the high frequency power signal (Continued)

of the magnetic coupling unit (702, 704) and of a magnetic coupling unit of the counterpart connector and/or ii) a received time calibration signal for determining and/or resetting the relative time difference.

14 Claims, 24 Drawing Sheets

(51) Int. Cl.
*H02J 50/10* (2016.01)
*A61B 5/00* (2006.01)

(56) References Cited

U.S. PATENT DOCUMENTS

| | | |
|---|---|---|
| 2008/0146925 A1 | 6/2008 | Byrd et al. |
| 2011/0002324 A1 | 1/2011 | Falck et al. |
| 2011/0217923 A1* | 9/2011 | Ma ..................... A61B 34/30 455/39 |
| 2012/0029304 A1 | 2/2012 | Medina et al. |
| 2015/0263785 A1 | 9/2015 | Farrokhi et al. |

OTHER PUBLICATIONS

Plomp, J. et al., "Considerations for Synchrononization in Body Area Networks for Human Activity Monitoring", Int J Wireless Info Networks 18 (2011): 280-294. DOI 10.1007/s10776-011-0136-2.

* cited by examiner

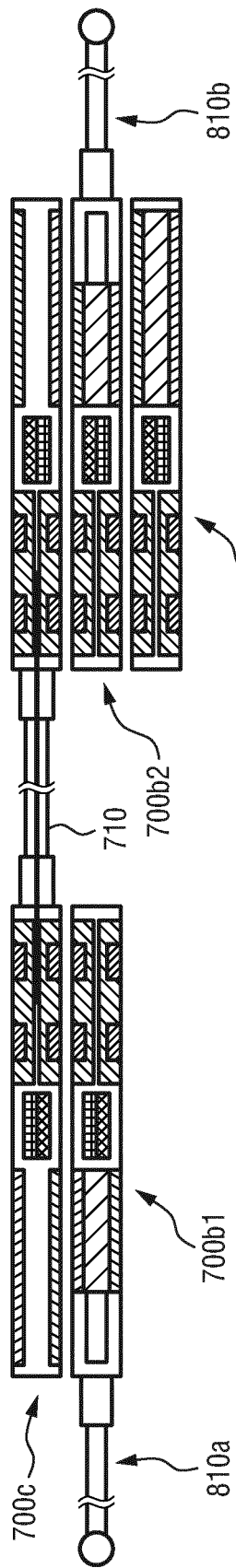
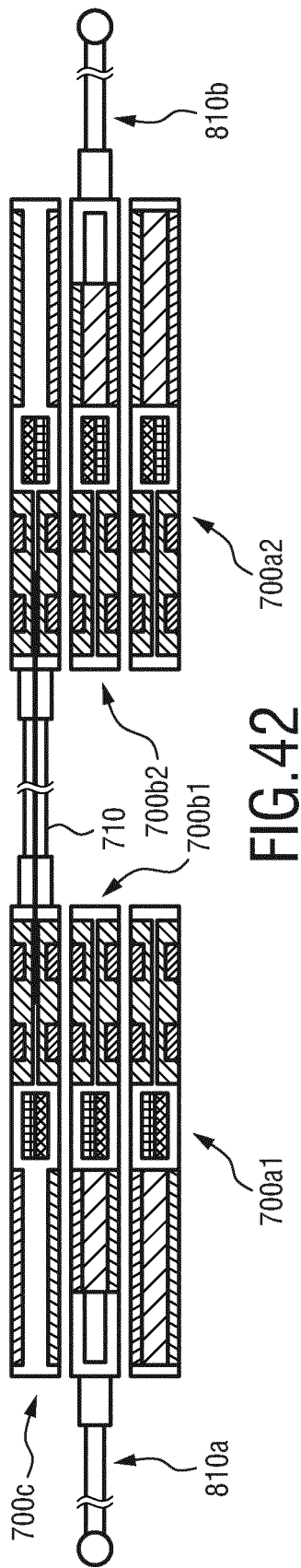
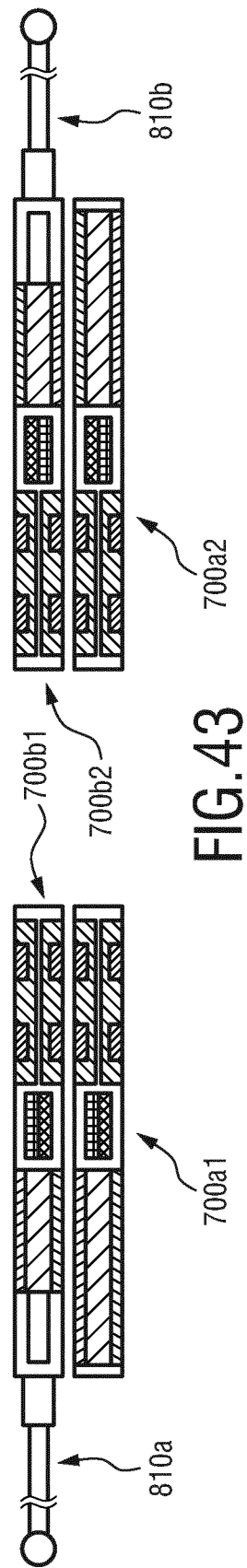
FIG. 41
FIG. 42
FIG. 43

DEVICE FOR WIRELESS TRANSMISSION OF DATA AND/OR POWER

CROSS-REFERENCE TO PRIOR APPLICATIONS

This application is the U.S. National Phase application under 35 U.S.C. § 371 of International Application No. PCT/EP2017/084572, filed on 24 Dec. 2017, which claims the benefit of European Patent Application No. 17150246.1, filed on 4 Jan. 2017. These applications are hereby incorporated by reference herein.

FIELD OF THE INVENTION

The present invention relates to a device for wireless transmission of data and/or power between the device and another device of a system, in particular of a patient monitoring system.

BACKGROUND OF THE INVENTION

Wireless charging or powering of devices in general is an established technique that is convenient to users. Wireless powering can also be used in harsh environments where corrosion or moisture might jeopardize functionality or safety when galvanic contacts are used. There are several standards for wireless power such as Qi, PMA, Rezense and WiPower, and the market is growing rapidly. These techniques are mostly used for charging a battery powered device (e.g. a mobile phone, a tablet computer, etc.). Charging of multiple devices is possible. For instance in the Qi standard power plates with many smaller coils are available, however the devices need to be precisely positioned adjacent to each other (in the horizontal plane).

High-end patient monitoring is expanding from its traditional application in the critical care arena (ICU, OR) towards lower acuity settings such as the general ward, hospital-to-home, connected primary care, etc. The success of the existing high-end products is due to the quality of the measurements, their modularity, the overall system connectivity, the user interface and its consistency (backwards compatibility) across the total product line. At the same time the value segment market is expanding rapidly to address emerging countries and lower acuity settings where low-cost is of prime concern. In these markets compromises may be made on modularity, connectivity and (sometimes) measurement quality.

In the lifestyle and sports arena also physiological measurements are used more and more (such as heart rate, respiration rate, SpO2).

In said new application spaces wearable (cordless) sensors, miniaturization and low-power are necessary. The basic requirements across all these segments are the same, namely excellent measurement quality compared with non-compromised electrical patient safety. The latter is strictly regulated in the IEC 60601 standard and dictates in a worst case scenario (direct connection to the heart) a 10 µA maximum leakage current, 4 kV isolation towards ground and 1.5 kV isolation between each of the measurements. Additionally, the patient monitor must be able to withstand high differential voltages introduced by a defibrillator and large RF voltages from a surgical knife.

Conventional isolation and protection concepts are based on inductive power couplers (transformers) and optical data couplers for data transport, next to maintaining sufficient creeping and clearance between PCBs and connector pins.

Synchronization of clocks in computer networks and sensor systems is a well-known problem and solutions are available for both centralized and distributed systems. Synchronization of vital sign waveforms in patient monitoring is a major challenge, where requirements are severe. It is important that for instance waves shown on the display correspond beat by beat. Moreover the delay from signal to signal (for instance ECG to Invasive Blood Pressure (IBP) is equally important as it may contain important clinical information. Recently continuous non-invasive blood pressure measurements have been proposed based on Pulse Arrival Time (PAT) or Pulse Transit Time (PTT). For these methods timing errors between sensors must be smaller than 1 ms. Generally speaking, monitoring applications require sub millisecond timing accuracy.

Present solutions often use one master clock and multiple slave clocks in the devices connected via a cabled network. Messages are sent via the network to synchronize clocks. It is not straightforward to apply such techniques in a wireless sensor system as is used in wearable patient monitoring devices. Sometimes a master clock signal is transmitted but timing accuracy is typically a few ms to 100's of ms depending on the radio standard. Although much better timing sync is in principle possible for a radio (like Wi-Fi or Bluetooth (BT) micro second time stamps synchronization) such accuracy can only be reached with dedicated low-level implementation, not on top of a regular radio protocol implementation. Furthermore, the modules generally each have a separate module clock with its own drift. This requires calibration at regular intervals.

Other methods rely on the emission of a common time stamp signal and then derive timing signals locally in the devices based on their own local crystal oscillator. However, many standard radio protocol implementations do not allow synchronization at sub-millisecond accuracy, and in practical wearable applications the radio link may not always be available, while the medical application still requires continuous local signal synchronization.

Hence, there is a need for a solution that meets stringent relative time errors, for instance for a sensor system comprising dielectrically isolated nodes with only one power source. Moreover, there is a need for a solution that requires only minimal increase in complexity to achieve the required specifications (i.e. drifts less than 1 ms) over a period of several hours or days.

US 2007/0254726 A1 discloses an apparatus including a wireless transmitter modulating a carrier wave by transmission data and wirelessly communicating a signal, a wireless receiver mixing the wireless transmitter signal and a carrier wave and receiving the transmission data, a power carrier wave clock generator provided on one of the wireless transmitter and receiver generating a power carrier wave clock, a non-contact power transmitter transmitting power between the wireless transmitter and receiver through electromagnetic induction from the power carrier wave clock, a carrier wave generator mounted on the one of the wireless transmitter or receiver, and generating a carrier wave based on the power carrier wave clock, and a carrier wave reproducer mounted on the other of the wireless transmitter or receiver, and reproducing a carrier wave having the same frequency as the carrier wave based on a clock having the same frequency as the power carrier wave clock.

SUMMARY OF THE INVENTION

It is an object of the present invention to provide a device for wireless transmission of data and/or power that meets stringent relative time errors at low complexity.

In a first aspect of the present invention a device for wireless transmission of data and/or power between the device and another device of a system, in particular of a patient monitoring system, is presented, said device comprising:
- a connector comprising a data transmission unit arranged for transmitting data to and/or receiving data from another device of the system having a counterpart connector, and a magnetic coupling unit for transmitting power to and/or receiving power from another device of the system having a counterpart connector by use of inductive coupling using a high frequency power signal,
- a detection unit for detecting coupling of a counterpart connector of another device of the system with the connector, and
- a control unit for using the detection that a counterpart connector of another device of the system has been coupled with the connector as a trigger to determine and/or reset a relative time difference between a clock signal used by the device and a clock signal of the other device using i) the high frequency power signal of the magnetic coupling unit and of a magnetic coupling unit of the counterpart connector and/or ii) a received time calibration signal for determining and/or resetting the relative time difference.

Preferred embodiments of the invention are defined in the dependent claims.

One element of the present invention includes the use of an automatic detection when e.g. a sensor node is added to the system. This moment in time can be detected rather precisely, e.g. with sub-ms accuracy in all nodes providing a highly accurate (sub-ms) common time stamp in each node. Another element of the present invention is to exploit the common high frequency signal (e.g. in the range of 100 kHz) to the nodes that is used to transfer power to the different nodes. For nodes that are not in close proximity a dielectrically isolated cable may be used for the power and wireless data transfer. Furthermore, a wireless message from the system master can be used for a time stamp for all nodes.

The present invention thus provides a solution that can meet stringent relative time errors for a sensor system comprising dielectrically isolated nodes with only one power source. Moreover, only minimal increase in complexity is needed to achieve desired specifications (e.g. drifts less than 1 ms) over a period of several hours or days.

Further, embodiments of the present invention address at least some of the drawbacks of using wireless data communication, e.g. in a clinical setting. Particularly in systems using wireless devices it is of prime concern to implement and maintain unambiguous coupling between the devices. For instance, in a patient monitoring system using wireless measurement modules, it is important to ensure a robust coupling mechanism for coupling of patient and devices, such as measurement modules and the patient monitoring device. Such a coupling mechanism is generally known as "pairing" or "association" and is generally not trivial to implement in crowded areas with many different kinds of devices, such as hospitals. Further, the transitions between care settings (e.g. from OR to ICU or recovery) should be seamless and unambiguous, without any disturbance of the clinical workflow. Furthermore, patient re-location or mobile patients (in a ward or at home) are another challenge to solve.

In an embodiment the detection unit is configured to detect coupling of a counterpart connector in a magnetic, electric or optical manner. The way of detecting coupling is not essential, but can be chosen according to the circumstances and the application. These different ways of detection include NFC and Bluetooth as useful options.

The detection unit may be configured to detect coupling of a counterpart connector by detecting if the strength of magnetic coupling (often referred to as magnetic coupling factor k ($0<=k<=1$)) between the magnetic coupling unit and a magnetic coupling unit of the counterpart connector exceeds a magnetic coupling threshold, in particular by detecting impedance, resonance frequency and/or induced voltage for detecting the strength of magnetic coupling and/or by detecting if the intensity of data received by the data transmission unit from a data transmission unit of the other device exceeds an intensity threshold, in particular by detecting signal intensity and/or antenna impedance of an antenna of the data transmission unit for detecting the intensity of received data.

In case components are already connected, this is clear from the availability of power and strong RF signal. Attachment of a new component may be detected by use a polling mechanism to check the increase of magnetic coupling (and, optionally, an RF signal used for data transmission. Detection of disconnecting components may be performed by the inverse process: a polling mechanism to measure a decrease of the strength of magnetic coupling by use e.g. of impedance, resonance frequency and/or induced voltage (and, optionally, of the RF signal). Optionally, the RF signal strength may be measured in addition.

The device may further comprise a storage unit for storing the moment of detection that a counterpart connector of another device of the system has been coupled with the connector as a time stamp. The data transmission unit may then be configured to transmit the time stamp and/or a determined relative difference between the clock signal used by the device and the clock signal of the other device to the other device for storage in a master device of the system.

In another embodiment the other device comprises a battery, wherein the high frequency power signal used for transmitting power from the battery to the device is used for determining and/or resetting the relative time difference. Further, the device may also comprise a battery, wherein the control unit is configured to switch off the battery or generate a control signal for transmission to the other device for switching off the battery of the other device.

The present invention further enables that one of the device acts as a master not, i.e. the data transmission unit may be configured to receive a master clock signal from the other device or to transmit a master clock signal to the other device.

The device may further comprise a galvanic connection unit for galvanic coupling of the device to a third device having a counterpart galvanic connection unit and for receiving a master clock signal from the third device for calibrating the clock signal used by the device.

The device may further comprise a patient side connection unit for connecting the device to one or more sensors to receive one or more physiologic sensor signals, wherein the device is configured to calibrate the clock signal used by the device based on a periodicity of a received physiologic signal.

In various other embodiments the device may comprise a clock unit for generating the clock signal used by the device and/or a counter for counting the number of pulses of the high frequency power signal, wherein the counted number is used for calibrating the clock signal used by the device. The counter may hereby be configured to reset to zero when the device is coupled to or decoupled from another device or when the inductive coupling is interrupted or when an external synchronization event is detected.

The control unit may further be configured to decide if a received or generated high frequency power signal is transmitted to the other device or if a new high frequency power signal with different frequency and/or phase is regenerated. Also in this context the Qi standard may be used.

Still further, the data transmission unit may be configured for transmitting data by use of RF transmission, optical transmission, capacitive coupling or near field communication. The technology used for data transmission may e.g. be chosen according to the environment or application.

Preferably, RF transmission by use of an RF antenna is used. Hence, in a preferable embodiment the connector comprises a carrier, wherein said data transmission unit comprises an RF antenna arranged in or on the carrier and an RF circuit for driving the RF antenna and/or obtaining RF signals received by the RF antenna. The carrier may e.g. be a PCB.

Various designs of the RF antenna are generally possible. Preferred antenna designs include that the RF antenna is shaped in the form of a stripe, ring, planar inverted F or planar folded dipole. Further, the RF antenna is preferably arranged rotational symmetrically, which avoids the need for a predetermined rotational positioning of the connector with respect to a counterpart connector when connecting them. In an exemplary implementation a quarter wavelength planar inverted F-antenna may be used.

The magnetic coupling unit preferably comprises a flux concentrator for concentrating magnetic flux and one or more coils arranged around part of the flux concentrator. Thus, inductive coupling like in a transformer is preferably used for the transmission of power.

The flux concentrator may comprise a core shaped in the form of a C or E and/or may be arranged rotational symmetrically, which also supports avoiding the need for a predetermined rotational positioning of the connector with respect to a counterpart connector when connecting them.

Various designs of the flux concentrator and various numbers, designs and positions of the coils and the RF antenna(s) are generally possible according to the present invention, depending on the kind of application, the size, the costs, etc.

According to another embodiment the device may further comprise a data unit for generating and/or receiving data, and/or a power unit for supplying and/or consuming power. This e.g. enables processing of received data in the device itself.

The device according to the present invention may be coupled with a central monitoring device or hub (which may also be regarded as a device in the sense of the present invention) effectively forming a patient network. Many network topologies are generally known and can generally be used according to the present invention. Such topologies include for example Pico-nets and scatter nets described in the Bluetooth standard, whether or not combined with localization tracking and master/slave configurations.

Devices according to the present invention may include different classes of network components, in particular:
  measurement modules, battery modules, cable units;
  monitoring devices and hubs, connected to the hospital IT system, cloud, fog or DHP;
  storage devices (e.g. a wireless stick as temporary ID storage medium;
  wearable devices, such as a wristband or plaster worn by patients for identification, e.g. at a specific location.

BRIEF DESCRIPTION OF THE DRAWINGS

These and other aspects of the invention will be apparent from and elucidated with reference to the embodiment(s) described hereinafter. In the following drawings FIG. 41 shows a schematic diagram of a first embodiment of a system including different devices according to the present invention, FIG. 42 shows a schematic diagram of a second embodiment of a system including different devices according to the present invention, FIG. 43 shows a schematic diagram of a third embodiment of a system including different devices according to the present invention.

DETAILED DESCRIPTION OF EMBODIMENTS

Figure 1:
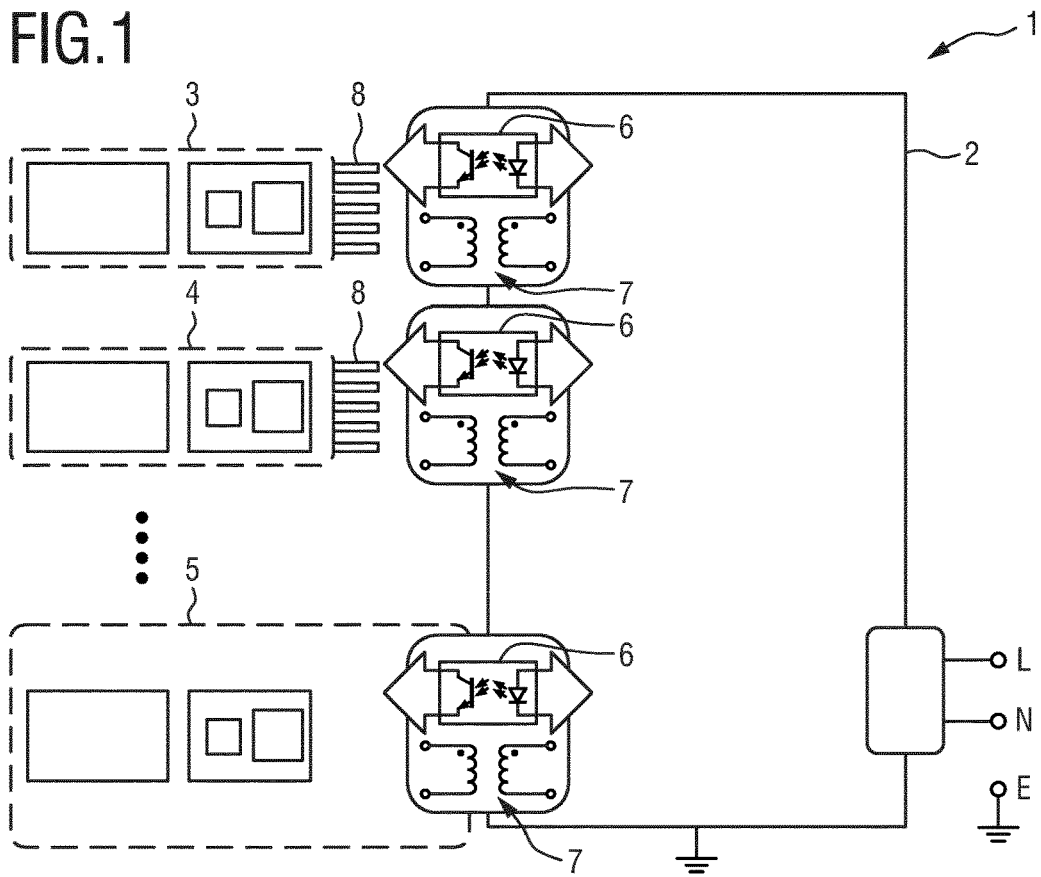
FIG. 1 shows a schematic diagram of a known system including a plurality of devices.

FIG. 1 shows a schematic diagram of a known system 1 including a plurality of devices 2, 3, 4, 5, which are configured to transmit power and data between them. Conventionally, a modular approach is used according to which measurement modules 3, 4 (representing one type of devices) are connected via expensive gold-plated mainboard connectors (i.e. via a galvanic connection) 8 to a central processing unit 2 (representing another type of devices), e.g. a central processor on a mainboard of a patient monitor. Further, an isolated measurement module 5 on the main board (representing another type of device) may be connected to the main processing unit 2 in the same way.

Some measurements may be implemented directly on the mainboard itself. Measurements are e.g. isolated from each other by using optocouplers 6 for data transmission and a transformer 7 for power transmission. All metal parts share the same (protected) earth connection; the measurements themselves are isolated from earth. Each measurement module 3, 4, 5 may be connected, generally via a cable, to one or more sensors (not shown), e.g. a pulse oximetry sensor, an accelerometer, ECG electrodes, that are placed at the patient's body.

In such a system electrical isolation involves a large part (at least 30%) of the measurement costs. Further, mainboard connectors are expensive and mechanically complex and cleaning is a challenge. Lowering the costs is a strong requirement in the value segment and lower acuity settings. Modularity is a strong requirement in high-end markets, and somewhat less in lower acuity and value segment markets. Wearable (cordless) sensors and low-power are important for lower acuity care settings. Further, aligning measurement concepts across the product range of a company lowers costs and maintains the same quality for all market segments.

Thus, there is a strong need for a low-cost, low-power, flexible and modular architecture, which is universally applicable to all patient monitoring settings or, more generally, to all systems comprising a plurality of (different and/or identical devices) in which power and/or data need to be transmitted under some or all of the above constraints.

Figure 2:
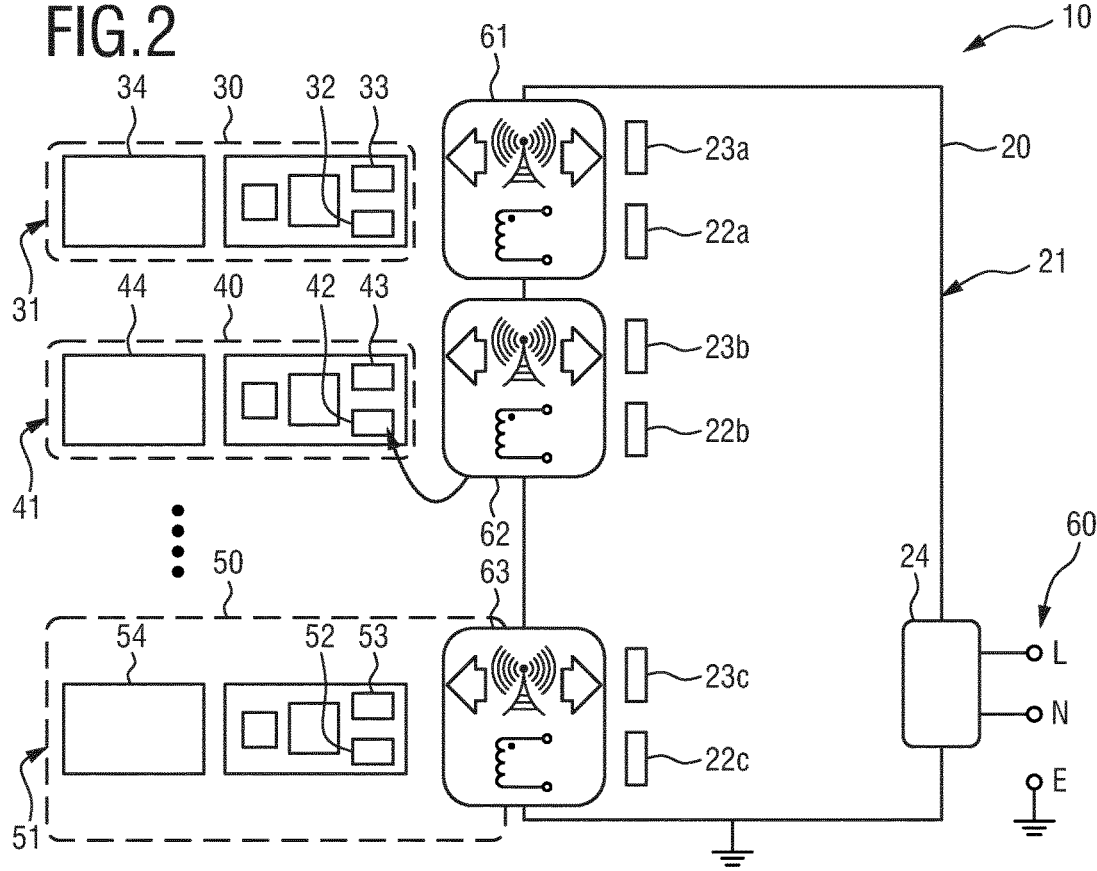
FIG. 2 shows a schematic diagram of a first embodiment of a system including a plurality of devices, FIG. 3 schematically shows a first embodiment of a connector for use in the system, FIG. 4 schematically shows a second embodiment of a connector for use in the system, FIG. 5 schematically shows a third embodiment of a connector for use in the system, FIG. 6 schematically shows a fourth embodiment of a connector for use in the system, FIG. 7 schematically shows a fifth embodiment of a connector for use in the system.

FIG. 2 shows a schematic diagram of a first embodiment of a system 10 including a plurality of devices 20, 30, 40, 50. According to the embodiment the devices 30, 40, 50 (e.g. representing measurement modules 30, 40, 50) are each connected in a wireless manner to the central processing unit 20, e.g. a patient monitor. Measurement modules, for instance in a patient monitoring system, are connected to the central processing unit 20 by individual magnetically coupled power transfer and near field contactless data transfer (whereby there may also be devices which only provide means for either magnetically coupled power transfer or near field contactless data transfer). This flexible architecture complies with the following applications of physiological measurements: measurement modules located on the main board (i.e. in the central processing unit 10), modular 'plug-in' measurement modules, measurement modules located in a mobile measurement server connected to the central processing unit 10, and cordless measurement modules. Generally, such measurement modules are galvanically insulated from each other. Measurement modules may also be combined in one single mechanical enclosure, and they may be fully galvanically insulated via their own coils.

Magnetic power coupling may e.g. be integrated in tracks of the (mainboard) PCB or implemented as magnetic coils in each of the two distinct parts of a connector for connecting two devices.

Contactless data transfer between two devices is preferably achieved via near-field communications means, e.g. Bluetooth 4.0 (low energy), Wi-Fi, ZigBee, NFC, capacitive (e.g. via the parasitic capacitance of the magnetic coupling) or optical, wherein radio transfer is the preferred option.

Preferably a (e.g. standardized) radio protocol is used to be compliant with all four applications mentioned, e.g. BLE, which is already integrated in many Commercial-Of-The-Shelf (COTS) components. Basically, in case the radiation field is confined within a certain volume (e.g. inside the housing of the monitor) any non-regulated radio protocol can be used.

Generally, each device that shall be able to transmit data and power in a cordless manner comprises a housing, a magnetic coupling unit arranged within the housing for transmitting power to and/or receiving power from another device of the system having a counterpart connector by use of inductive coupling, and a data transmission unit arranged for transmitting data to and/or receiving data from another device of the system having a counterpart connector, in particular by use of RF transmission, optical transmission, capacitive coupling or near field communication.

The measurement modules 30, 40 each comprise a housing 31, 41, a magnetic coupling unit 32, 42 and a data transmission unit 33, 43. Further, each of them comprises a patient side connection unit (PSC) 34, 44 for (generally in a galvanic manner) connecting the respective measurement module 30, 40 to a sensor or electrode (not shown) in order to receive data signals from the sensor or electrode and/or transmit control signals to the sensor or electrode. Optionally, further means for analog processing and/or digital processing may be provided, and a measurement module could contain a small energy buffer (e.g. a battery or super-capacitor) to bridge the transition time between wired-wireless scenarios as well as during battery replacement.

The isolated measurement module 50, i.e. a measurement module integrated on the main board of the patient monitoring device, comprises a housing 51, a magnetic coupling unit 52 and a data transmission unit 53. Further, it comprises a patient side connection unit (PSC) 54 as well.

The central processing unit 20 comprises a housing 21, several magnetic coupling units 22, 22a, 22c and several data transmission units 23, 23a, 23b, which may also be combined into a single data transmission unit, wherein a magnetic coupling unit and a data coupling unit form a connection module for connecting one (external) device to the central processing unit 20. Further, it comprises a supply terminal 24 comprising an isolation barrier for coupling the central processing unit 20 to an external power supply 60. Furthermore, the central processing unit 20 generally contains all the hardware needed for power and voltage generation, control, input/output, display and central processing of data from measurements and alarm generation.

The ability to transmit data and power between two devices of the system 10 is indicated through blocks 61, 62, 63. It should be noted that the system 10 may also comprises devices, which are not configured for transmitting and receiving data and power, but which are configured to only transmit data and/or power or which are configured to only receive data and/or power.

Figure 3:
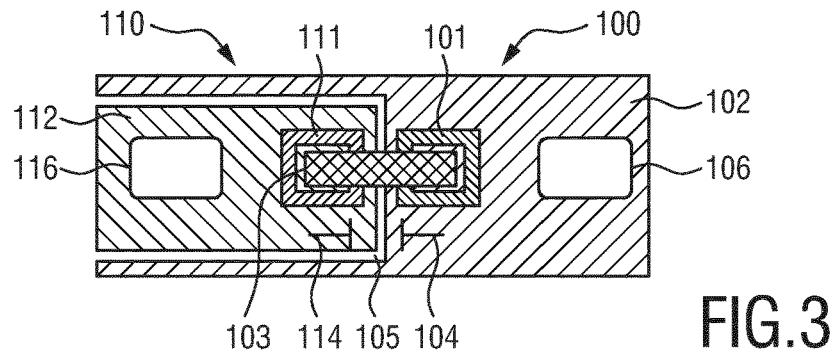

A first embodiment of a connector 100, 110 for wireless transmission of data and/or power between separate devices comprising such a connector is schematically shown in a top view in FIG. 3. These connectors 100 (e.g. of a central processing unit) and 110 (e.g. of a measurement module) represent a low-cost solution and can be implemented on-board. The tracks of a PCB 102, 112 may be used as transformer windings (i.e. coils) 101 (e.g. representing a primary coil), 111 (e.g. representing a secondary coil), separated in the horizontal and/or the vertical direction. Magnetic coupling may be enhanced by adding a flux concentrator 103, e.g. a ferromagnetic core having two legs (each carrying one of the coils 101, 111) and two yokes connecting the two legs to form a ring (which need not necessarily circular, but may also have other shapes such as rectangular, elliptical, etc. RF antennas 104, 114 are integrated on the PCBs 102, 112 as well. A gap 105 between the connectors 100, 110 provides an isolation barrier. A mainboard processor 106 may be provided in the central processing unit and a measurement unit 116 may be provided on the measurement module.

Figure 4:
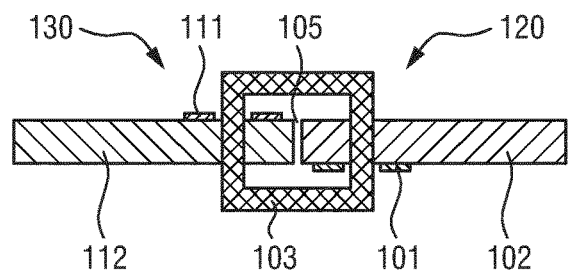

FIG. 4 schematically shows a cross-sectional view of a second embodiment of a connector 120, 130 for use in the system providing isolated measurement on the mainboard of the central processing unit. The coils 101, 111 are located on different surfaces of the respective PCB 102, 112 and are magnetically coupled via a flux concentrator 103.

Figure 5:
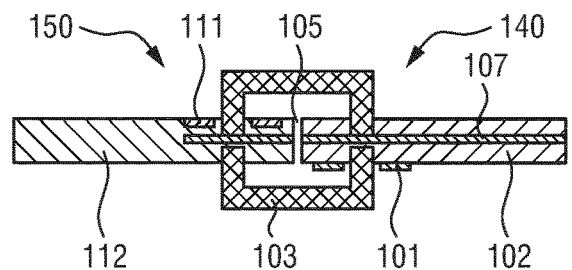
Figure 6:
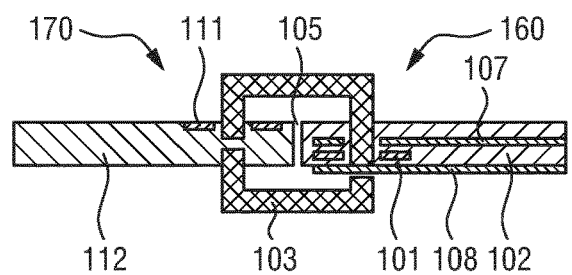

Obviously, many variations on this approach are feasible. FIG. 5 schematically shows a cross-sectional view of a third embodiment of a connector 140, 150 for use in the system. In this embodiment a third in-between layer 107 is provided, which is arranged within the PCB 102, in vertical direction, on a height level in between the coil 101 and the coil 111. The third in-between layer 107 is connected to ground to reduce stray capacitive coupling between the coils 101, 111. Further layers, such as another ground layer 108, may be added for EMC reasons, as shown in FIG. 6 depicting a fourth embodiment of a connector 160, 170 for use in the system.

Figure 7:
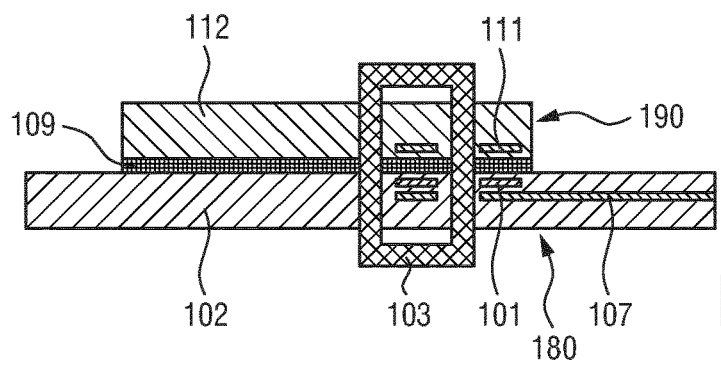

FIG. 7 schematically shows a cross-sectional view of a fifth embodiment of a connector 180, 190 for use in the system. In this embodiment the measurement PCB 112 is located on top of the mainboard PCB 102 with an insulation foil 109 in between and magnetically coupling via the flux concentrator 103.

In still another variation of one of the above described embodiments the secondary coil may be integrated on the die or in the package of an ASIC, which comprise the electronic circuitry of the measurement.

Preferably, the main microprocessor on the central processing unit controls or drives the primary coil of the transformer. The AC voltage of the secondary coil is rectified and stabilized to supply the measurement module. This approach may make use of the Qi standard (or other standard) of wireless charging, and the arrangement and construction of the components can generally be made to fulfill requirements of one or more of these standards (e.g. the coils should be close to the surface). Alternative methods may, however, also be used, and e.g. the AC voltage may be passed to the measurement module.

For data communication the central processing unit may comprise a near field radio-stack, communicating with the isolated measurements via e.g. Bluetooth Low Energy, ZigBee or in any other suitable way. Every non-standard protocol is allowed in case the radiation is limited to a confined housing.

RF transmission may be achieved via separate antennas, via capacitive coupling pads or even via the parasitic capacitance of the transformer coils. Said parasitic capacitance should be kept very small to be compliant with the IEC 60601-2-49 standard isolation requirements, but this constraint is e.g. achievable with transmission in the UHF radio band of 2.4 GHz or beyond.

Figure 8:
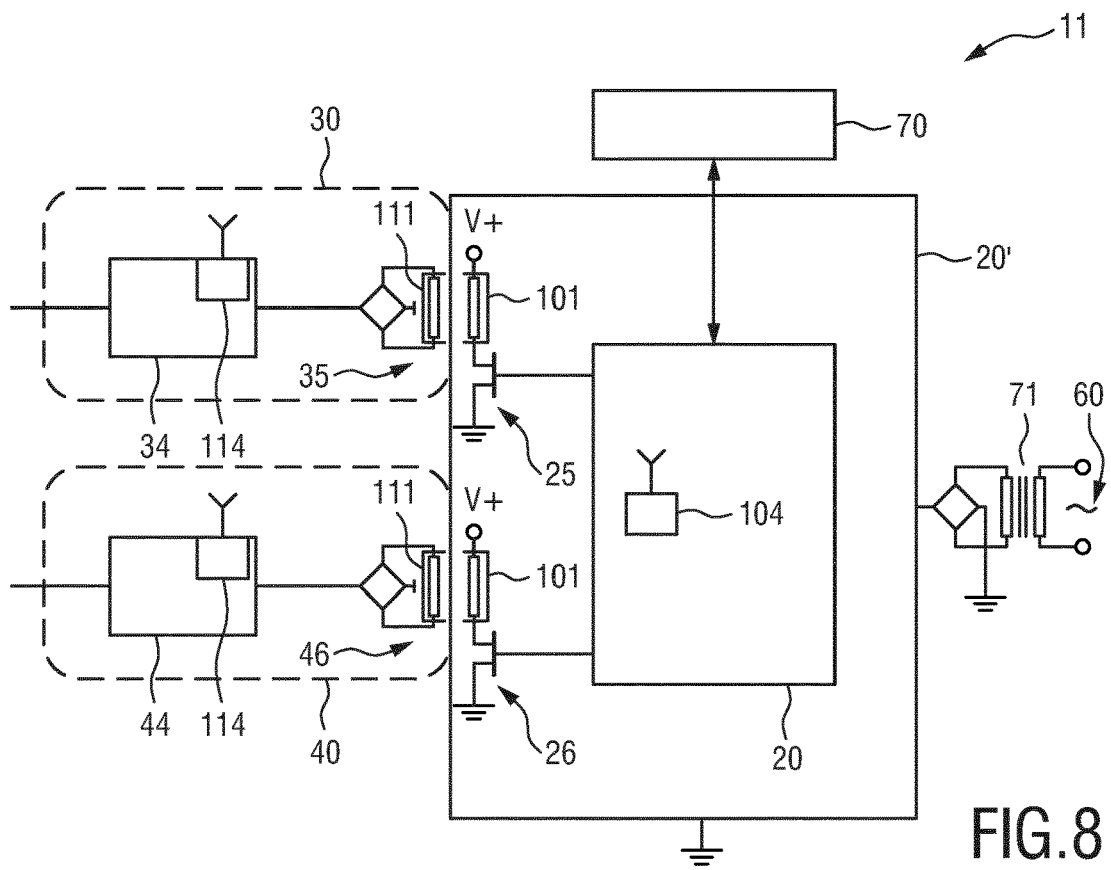
FIG. 8 shows a schematic diagram of a second embodiment of a system.

FIG. 8 shows a schematic diagram of a second embodiment of a system 11 including a plurality of devices 20, 30, 40. In this embodiment the one or more measurement modules 30, 40 are e.g. fitted in a measurement rack 20' and are coupled to the central processing unit 20 by magnetic connectors 25, 35 (for the module 30) and 26, 46 (for the module 40) comprising a primary coil 101 of the central processing unit 20 in close proximity to a secondary coil 111 and RF antenna 114 of the modules 30, 40. For data transmission an RF antenna 104 may be provided in the central processing unit 20 and a corresponding RF antenna 114 may be provided in the measurement modules 30, 50 (e.g. an antenna used in near-field mode for bridging small distances, such as BT, ZigBee, NFC, etc.

Due to the absence of pins, cleaning is easy. Hence, these connectors 25, 35, 26, 46 replace the expensive and cumbersome cleanable galvanic connectors as conventionally used and as shown in FIG. 1. Further, PSC units 34, 44 may be provided for connection to respective sensors, e.g. a temperature sensor or a SpO2 sensor.

The system may further comprise a user interface 70 coupled to the central processing unit 20, e.g. comprising one or more displays, buttons, switches, etc. Further, a mains power transformer 71 may be provided for connection to a mains power supply 60.

Measurements may be located inside a detachable small box (not shown), also called measurement server, close to the patient, which is connected to the patient monitor via a cable comprising connectors as disclosed herein or via a wireless link, so that it can be operated in a hybrid mode (i.e. in wired or wireless way). Within such a measurement server every measurement's battery will be charged during normal use. Whenever a patient needs to be moved, the link to the patient monitor might be lost for a certain amount of time; nevertheless the individual measurements will continue to measure, record and process all the vital signs. Hence, no important data regarding the patient's health status is lost. Again, in the vicinity of a patient monitor, the data might be synchronized again with a central server.

Figure 9:
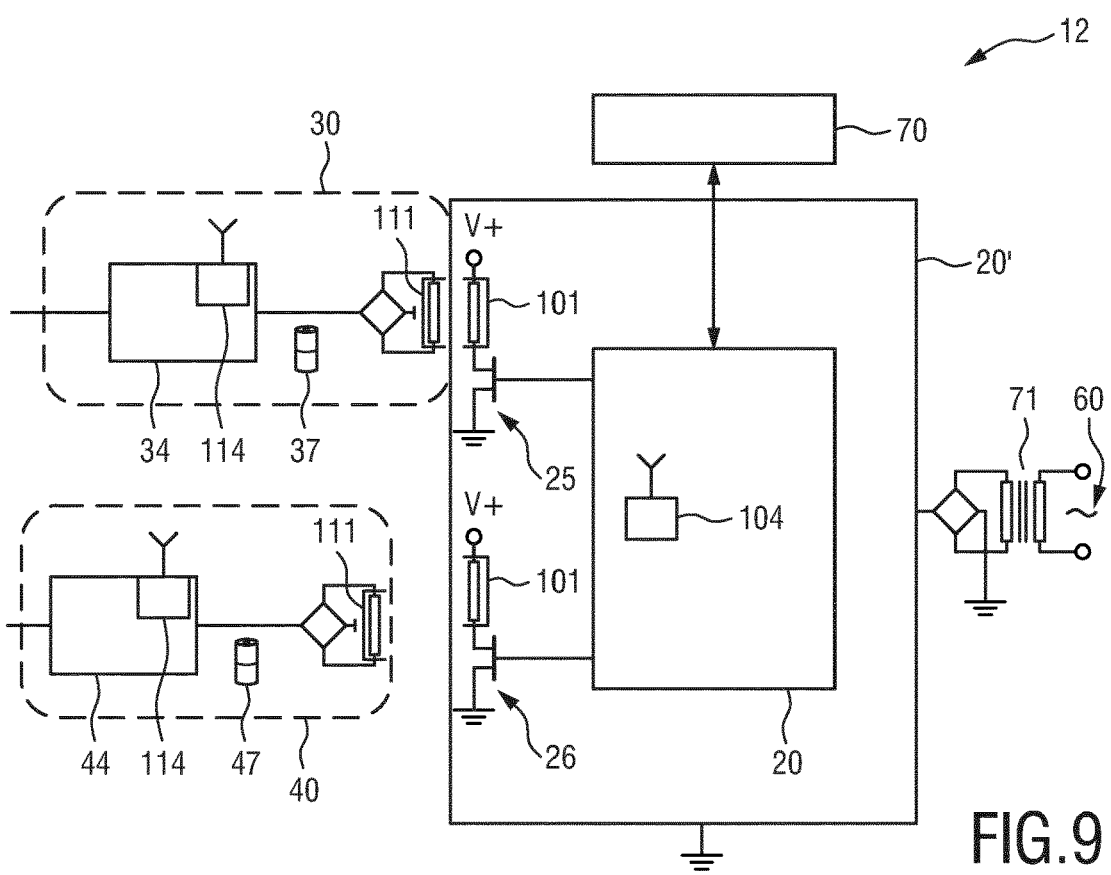
FIG. 9 shows a schematic diagram of a third embodiment of a system, FIGS. 10A and 10B schematically show a cross-sectional view and a top view respectively of sixth embodiment of a connector for use in the system, FIG. 10C schematically shows a sixth embodiment of a connector for use in the system in the connected state, coupled to a counterpart connector, FIG. 11 schematically shows a seventh embodiment of a connector for use in the system, FIGS. 12A and 12B schematically show a cross-sectional view and a top view respectively of an eighth embodiment of a connector for use in the system, FIGS. 13A and 13B schematically show a cross-sectional view and a top view respectively of a ninth embodiment of a connector for use in the system, FIGS. 14A and 14B schematically show a cross-sectional view and a top view respectively of a tenth embodiment of a connector for use in the system, FIG. 15 schematically shows an eleventh embodiment of a connector for use in the system, FIG. 16 schematically shows the layout of a connector with automatic switching between modes, FIGS. 17A, 17B, 17C, and 17D schematically show a cross-sectional view, a top view, and first and second perspective views respectively of a first embodiment of a stackable connector for use in the system, FIGS. 18A, 18B, and 18C schematically show a cross-sectional view, and first and second perspective views respectively of a stack of two connectors according to the first embodiment, FIG. 19 schematically shows a stack of three connectors according to the first embodiment, FIGS. 20A, 20B, and 20C schematically show arrangements of several devices in the form of a daisy chain, each device including one or more of the connectors according to the invention, FIGS. 21A and 21B schematically show a cross-sectional view and a top view respectively of a second embodiment of a stackable connector for use in the system, FIGS. 22A and 22B schematically show a cross-sectional view and a top view respectively of a third embodiment of a stackable connector for use in the system, FIGS. 23A, 23B, and 23C schematically show a cross-sectional view, a top view, and a simplified cross-sectional view respectively of a fourth embodiment of a stackable connector for use in the system, FIG. 24 schematically shows a fifth embodiment of a stackable connector for use in the system, FIGS. 25A and 25B schematically show a cross-sectional view and a top view respectively of a sixth embodiment of a stackable connector for use in the system, FIGS. 26A and 26B schematically show a cross-sectional view and a top view respectively of an embodiment of a connector for use in the system having a lateral geometry, FIGS. 27A and 27B schematically show a cross-sectional view and a top view respectively of a daisy chain using connectors as shown in FIGS. 26A and 26B, FIGS. 28A and 28B schematically show a cross-sectional view and a top view respectively of a body worn sensor arrangement using connectors as shown in FIGS. 26A and 26B, FIG. 29 schematically shows the coupling of different modules and units to a patient monitor using connectors as shown in FIGS. 26A and 26B.

By putting in an additional re-chargeable battery 37, 47 into the measurement modules 30, 40, as shown in FIG. 9 showing another embodiment of a system 12, the autonomous operation of said measurement modules is possible. When re-fitted into the measurement rack the battery is charged via the magnetic coupling. Battery management is at the measurement module and may (optionally, but not preferably) be made according to the Qi standard for wireless charging.

Data transfer preferably complies with existing connectivity standards. For example when using the Bluetooth LE 4.0 radio, the patient monitor becomes direct applicable for the Continua Health Alliance, which is a non-profit open industry organization of healthcare and technology companies joining together in collaboration to improve the quality of personal healthcare. The Continua Health Alliance is dedicated to establishing a system of interoperable personal connected health solutions with the knowledge that extending those solutions into the home fosters independence empowers individuals and provides the opportunity for truly personalized health and wellness management. These aims are supported by the present invention.

FIGS. 10 to 15 show further embodiments of a connector.

Figure 10A:
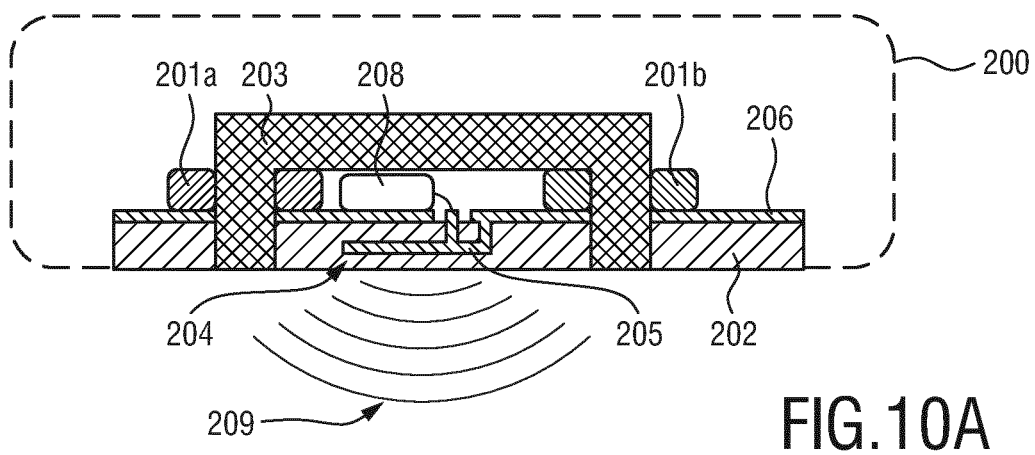
Figure 10B:
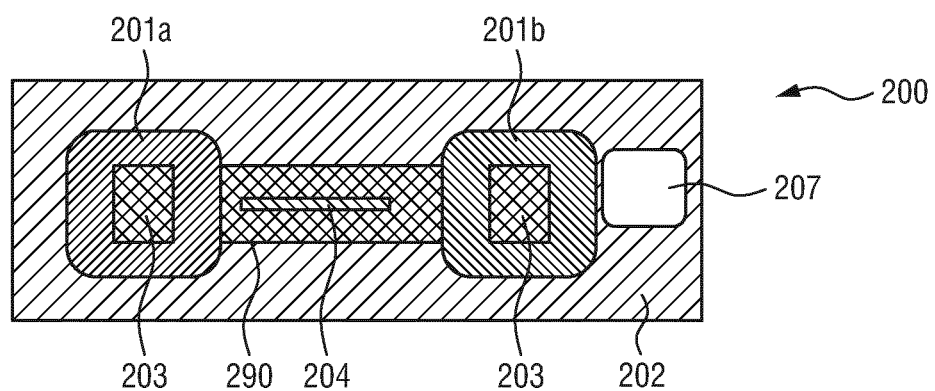

FIG. 10 schematically shows a cross-sectional view (FIG. 10A) and a top view (FIG. 10B) of a sixth embodiment of a connector 200 for use in the system in an unconnected state. The connector 200 comprises a PCB 202, which comprises a quarter wavelength planar inverted F-antenna (PIFA) 204 as part of the data transmission unit integrated in the tracks 290. The RF antenna 204 is formed by an RF signal line 205 and a ground plane 206. The magnetic field is generated by coils 201a, 201b wrapped around the C-shaped (also called U-shaped) flux concentrator 203 made from a material with high magnetic permeability for the frequencies of interest. Additional conducting sheet material may be added (as cover) to short the remaining stray field in the electronics by eddy currents. Additional cladding of the core 203 may help to shield the RF signal, which is a short-range radio field 209. When no other connector is attached (i.e. in the unconnected state), the RF antenna 204 operates in the far-field mode, wherein its directivity is pointed to the outside world as indicated in FIG. 10A.

A power unit 207 is coupled to the coils 201 for power supply to the coils 201 and/or power reception from the coils 201. An RF unit 208 is coupled to the RF antenna 204 for data supply to the RF antenna 204 and/or data reception from the RF antenna 204.

Figure 10C:
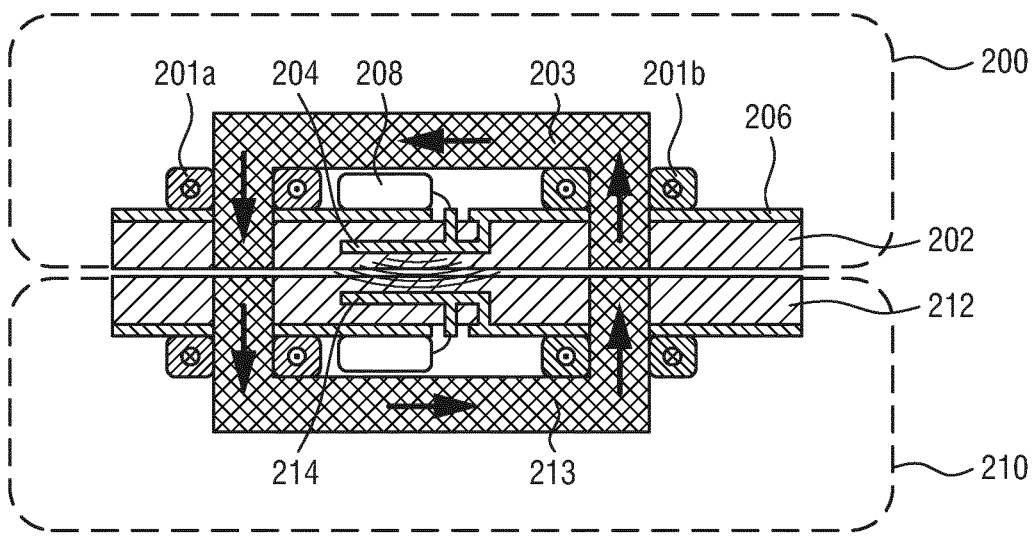

In the connected state, as illustrated in FIG. 10C showing the connector 200 coupled to a counterpart connector 210, the poles of both C-shaped flux concentrators 203, 213 and the antennas 204, 214 are almost perfectly aligned, so that the RF and magnetic fields are optimally coupled and shielded from the outside world.

Connecting induces two effects:

i) Firstly, the magnetic coupling increases dramatically, e.g. from k=0.5 to k>0.95, which may be detected directly (e.g. via the induced voltage) or indirectly (e.g. using proximity detection). Via a polling mechanism this effect is recognized by the magnetic powering electronics (e.g. Qi, PowerMat or custom) via the changed coil impedance, resonance frequency or induced voltage. In the unconnected state the magnetic powering is disabled, hence no interference is induced into the radio channel, in the measurement or in metal parts in close proximity. In the connected state, the flux is very well confined into the flux concentrators 203, 213, which also prevent interference. Disconnecting may be detected by polling the opposite effect (by briefly switching off the coil and observing the resulting effect).

ii) Secondly, due to the very short distance between the two antennas 204, 214, the amplitude and SNR of the received RF signals increases significantly. The radio transmitters can now scot-free switch to a near-field mode by lowering their output power while maintaining consistent data communication. Consequently, the radiated RF power in the neighborhood is significantly reduced, which helps to freeing-up the radio spectrum. Furthermore, due to the efficient RF coupling, the power consumption of the radio is reduced.

It should be noted that RF coupling in the near-field mode, in which the distance is a fraction of the wavelength, is more due to capacitive coupling than far field EM waves. Both effects are validated on a regularly basis via a polling mechanism, or triggered by additional proximity detection (optical, magnetic) or by a simple mechanical switch or a reed-switch.

To avoid stray flux a coil is preferably not powered fully (continuously) without counter-core present. However a polling mechanism may generate power for a short time (e.g. 10 ms) every second to measure magnetic coupling.

RF communication and/or data transfer via the magnetic coupling (as e.g. implemented in the Qi standard) or optical coupling is used to update and negotiate IDs, required power, signal quality, charging status etc. before deciding to start nominal power transfer.

Below it will be described in more detail how the actual connection/disconnection process triggers association in a patient network and how safety is implemented.

Galvanic isolation is guaranteed by the PCB layer material and the C-core. Alternatively, extra isolation layers on top on the PCB 202, 212 and the pole-tips of the C-core 203, 213 can be added. The unoccupied area of the PCB may be used for the measurement electronic and the PSC. Ferrite cores can be good conductors, but there are also highly resistive (composite) ferrites available.

Figure 11:
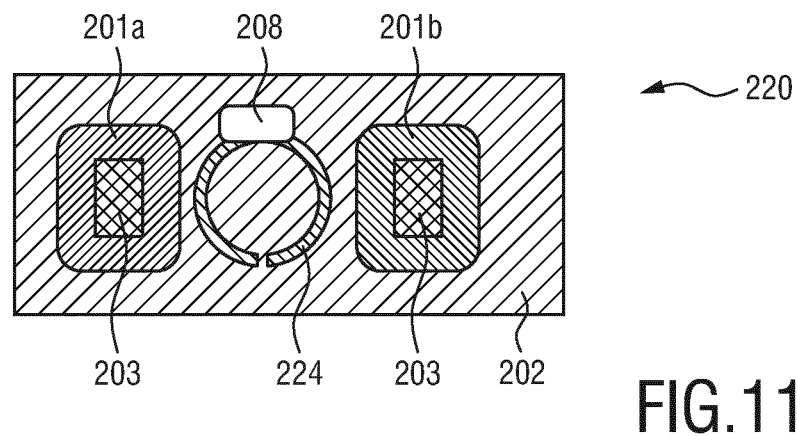

Alternative antenna configurations are possible, e.g. a ring shaped antenna 224 as shown in FIG. 11 depicting a top view of a seventh embodiment of a connector 220 for use in the system.

Figure 12A:
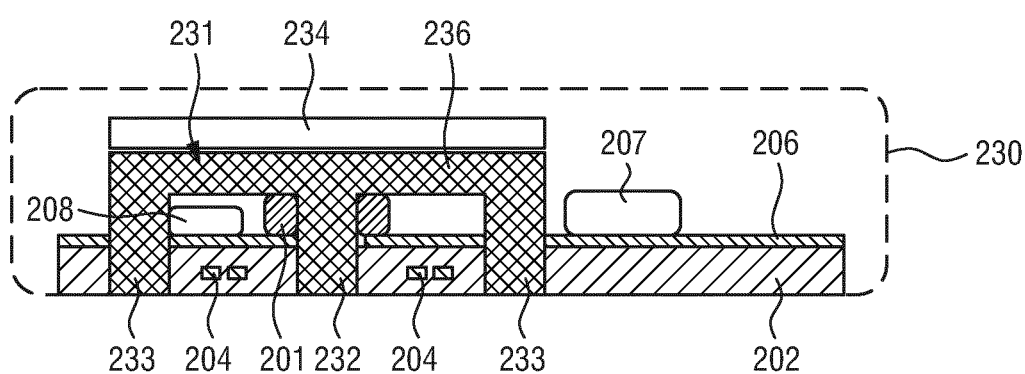
Figure 12B:
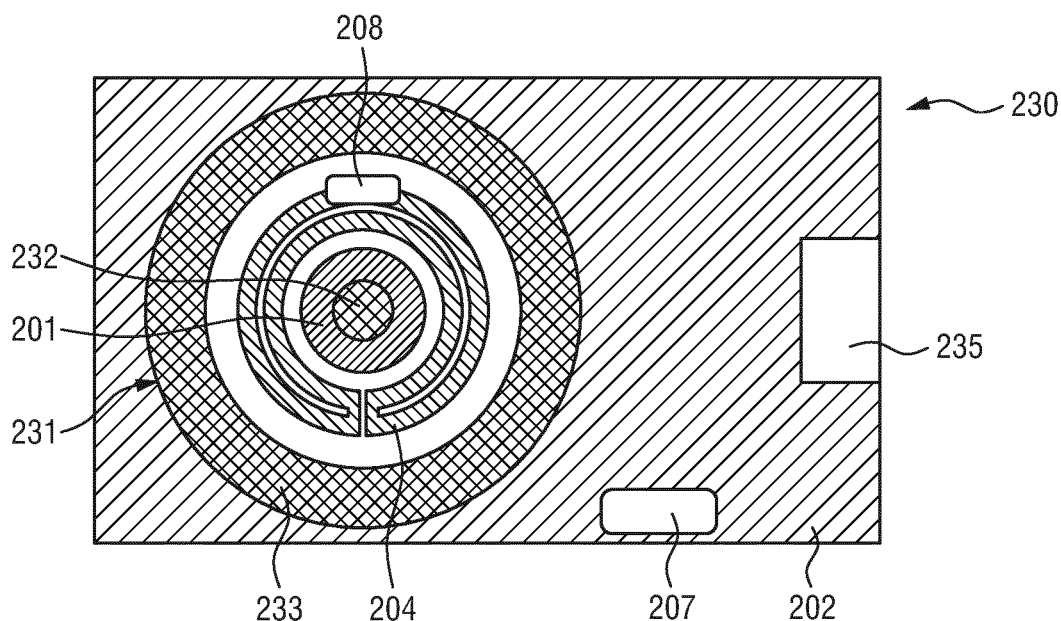

In the embodiments shown in FIGS. 10 and 11 the mechanical alignment of the connectors 200, 210, 220 is limited to two rotational orientations in which the antennas and C-cores are aligned. This is a serious drawback when using cables in body-worn measurements and daisy chain configurations. This problem is solved by a rotational symmetrical connector 230 as shown in FIG. 12 showing a cross-sectional view (FIG. 12A) and a top view (FIG. 12B) of an eighth embodiment of a connector 230 for use in the system.

The inner leg 232 of the E-core 231 (i.e. a core having a cross-section forming an E) carries the coil windings 201 for magnetic powering. The RF antenna 204 is arranged in the PCB 201 between the inner leg 232 and the outer legs 233 (which is actually a single ring as shown in FIG. 12B). The legs 232, 233 are connected by a yoke 236. The inner or outer walls of the core 231 may also be cladded with conductive material to further reduce interference. When two of such connectors are connected, the two halves form a pot-core where the magnetic field and the radio signals are thus very well coupled and shielded. In addition, a measurement unit 234 and a PCS unit 235 may be provided.

Figure 13A:
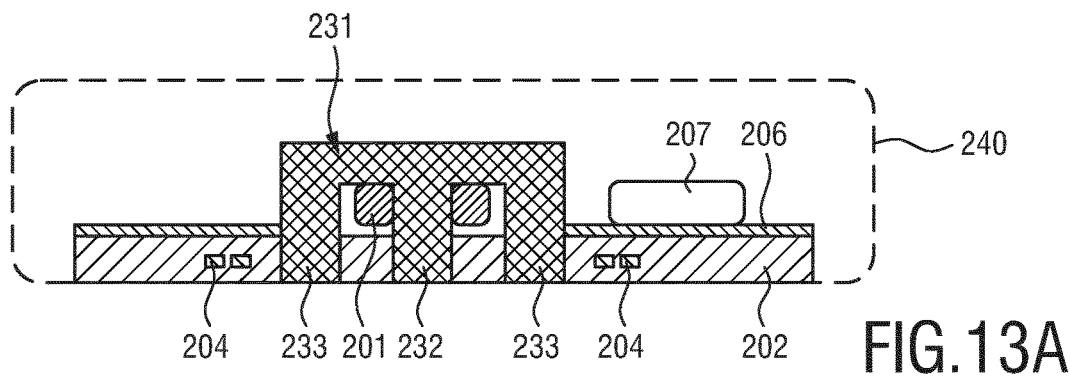
Figure 13B:
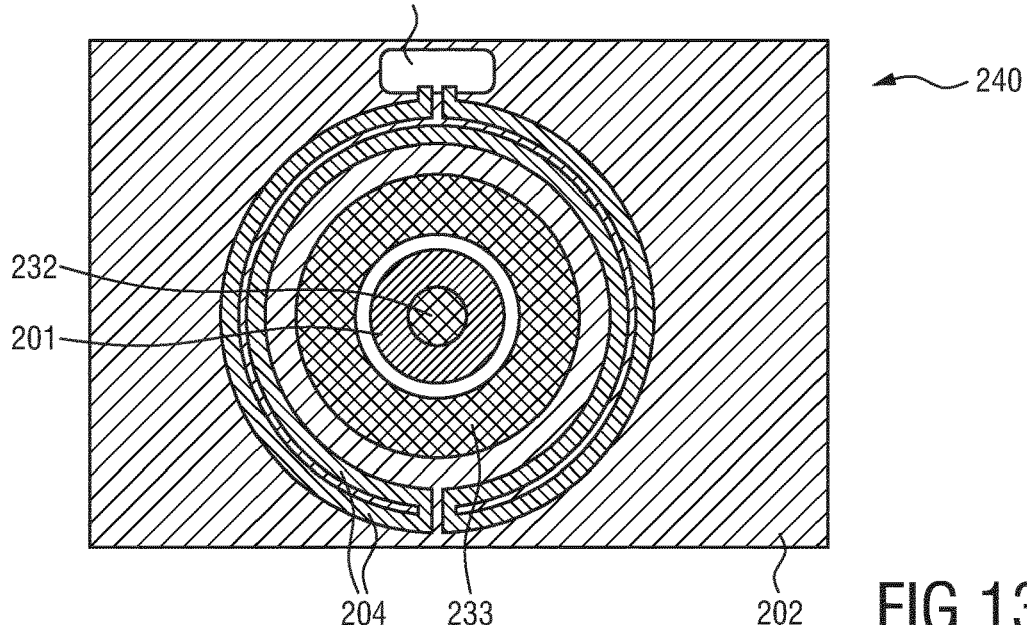

Alternatively, the RF antenna 204 is located outside the magnetic core 231, i.e. around the outer legs 233, which may contribute to even less crosstalk and interference between the RF and magnetic signals. This is illustrated in FIG. 13 showing a cross-sectional view (FIG. 13A) and a top view (FIG. 13B) of a ninth embodiment of a connector 240 for use in the system.

Figure 14A:
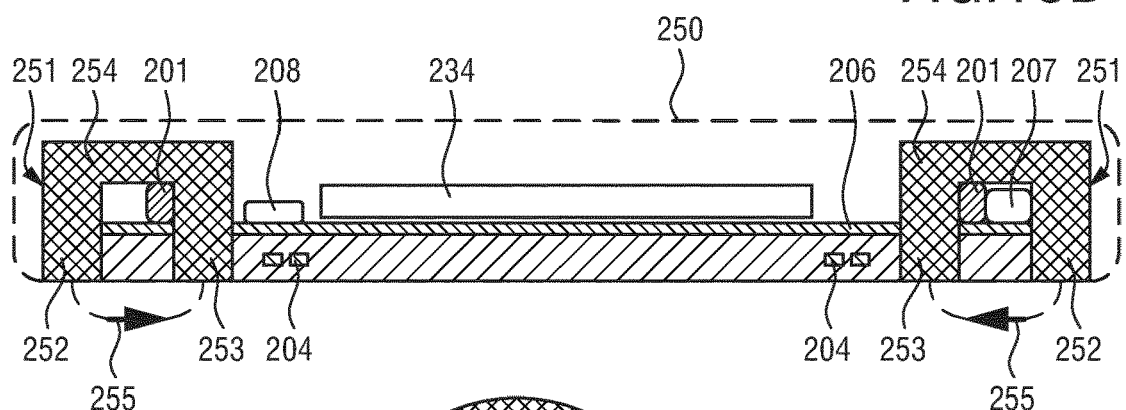
Figure 14B:
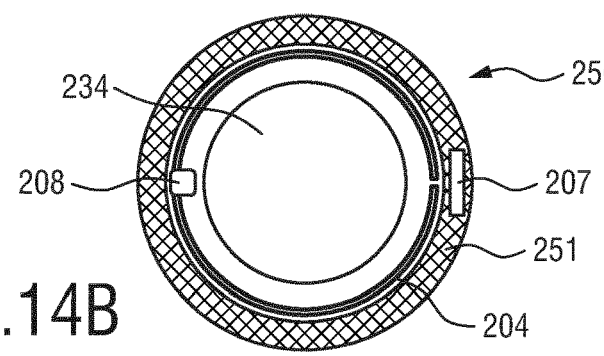

FIG. 14 shows a cross-sectional view (FIG. 14A) and a top view (FIG. 14B) of a tenth embodiment of a connector 250 for use in the system comprising a rotational symmetrical C-core 251 forming a ring having a C-shaped cross-section formed by two legs 252, 253 connected by a yoke 254. The magnetic flux generated by the coil 201 is indicated by arrows 255. The RF antenna 204 is arranged between the inner legs 252 of the C-core 251.

Figure 15:
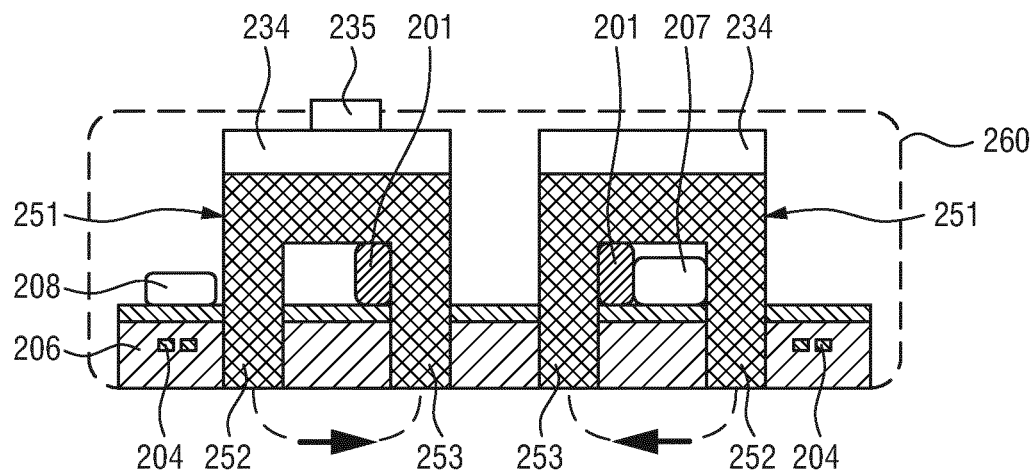

FIG. 15 shows a cross-sectional view of an eleventh embodiment of a connector 260 for use in the system, which is similar to the tenth embodiment shown in FIG. 14, but in which the RF antenna 204 is arranged around the outer legs 252 of the C-core 251.

The connectors shown in FIGS. 10 to 15 provide the advantage that they are rotational symmetrical and that—in connected state—there is a very small gap between the connector and its counterpart connector.

Figure 16:
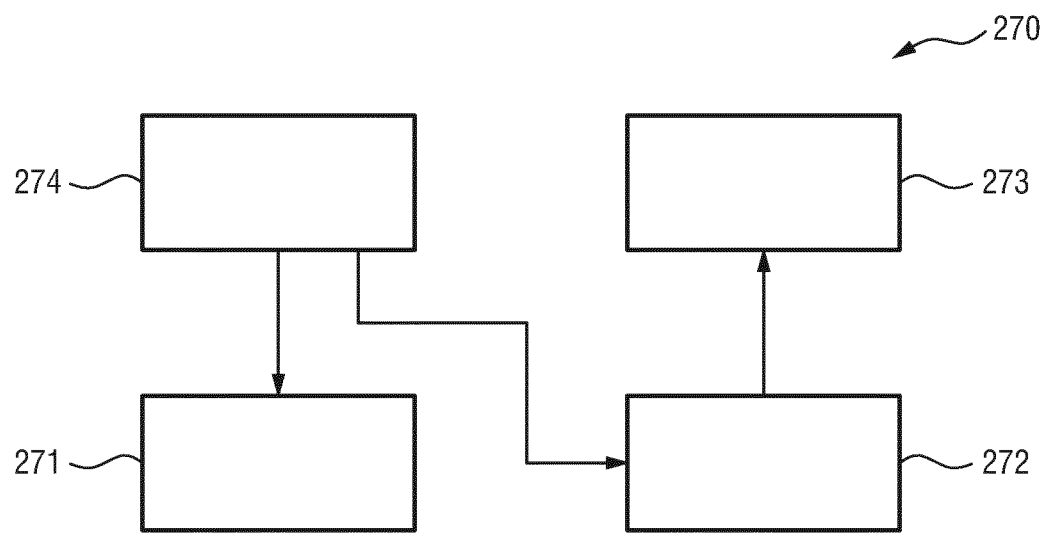

FIG. 16 schematically depicts the layout of a connector 270 (such as the connectors shown in FIGS. 10 to 15) for wireless transmission of data and/or power between separate devices comprising such a connector. The connector 270 comprises a data transmission unit 271 (e.g. comprising an RF antenna 204) arranged for transmitting data to and/or receiving data from another device of the system having a counterpart connector, preferably by use of RF transmission. The connector further comprises a magnetic coupling unit 272 (e.g. comprising a coil 201 and a core 203) for transmitting power to and/or receiving power from another device of the system having a counterpart connector by use of inductive coupling. A detection unit 273 (e.g. comprising a power unit 207) is provided for detecting the strength of magnetic coupling between the magnetic coupling unit 272 and a magnetic coupling unit of the counterpart connector. A control unit 274 switches the data transmission unit 201 into a low-power mode and/or enables the magnetic coupling unit 272, if the detected magnetic coupling is above a first threshold and/or its increase is above a second threshold. Further, the control unit 274 switches the data transmission unit 271 into a high-power mode and/or disables the magnetic coupling unit 272, if the detected magnetic coupling is below a third threshold and/or its decrease is above a fourth threshold. The thresholds may be predetermined, e.g. derived from a simulation or from measurements. This embodiment enables the automatic setting of the correct mode of the connector which particularly minimizes power consumption, crosstalk and usage of RF bandwidth.

It should be noted that the detection unit 273 and the control unit 274 disclosed in FIG. 16 may generally be used in all other connectors disclosed herein.

FIGS. 17 to 28 show a plurality of embodiments of a stackable connector for explaining details of such a stackable connector.

Figure 17A:
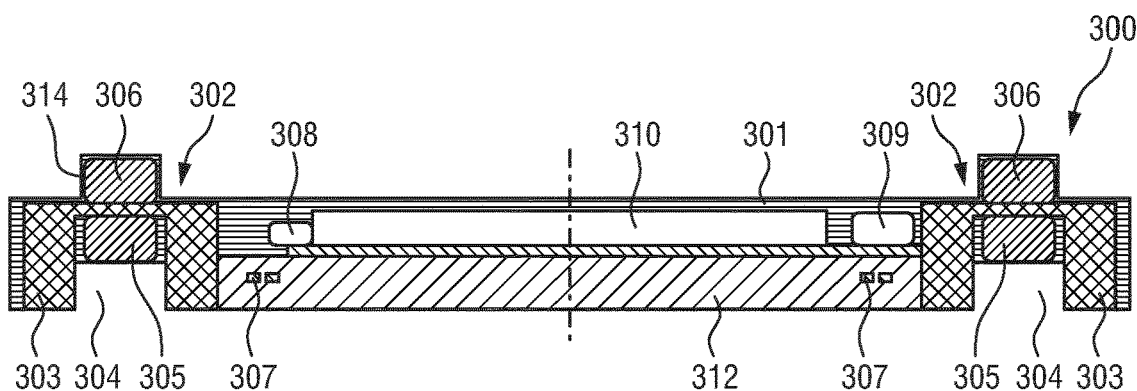
Figure 17B:
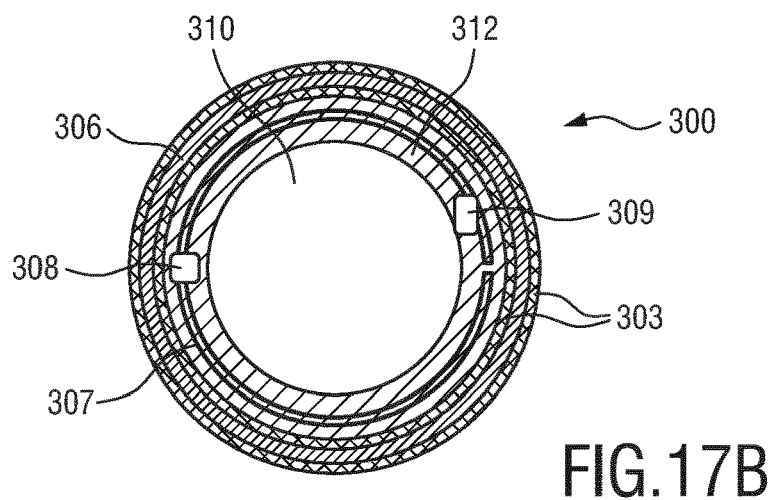
Figure 17C:
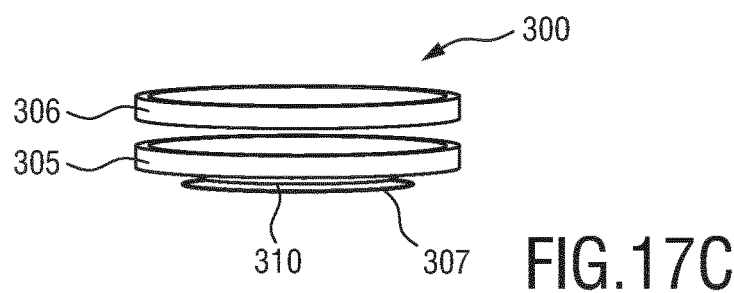
Figure 17D:
Figure 18A:
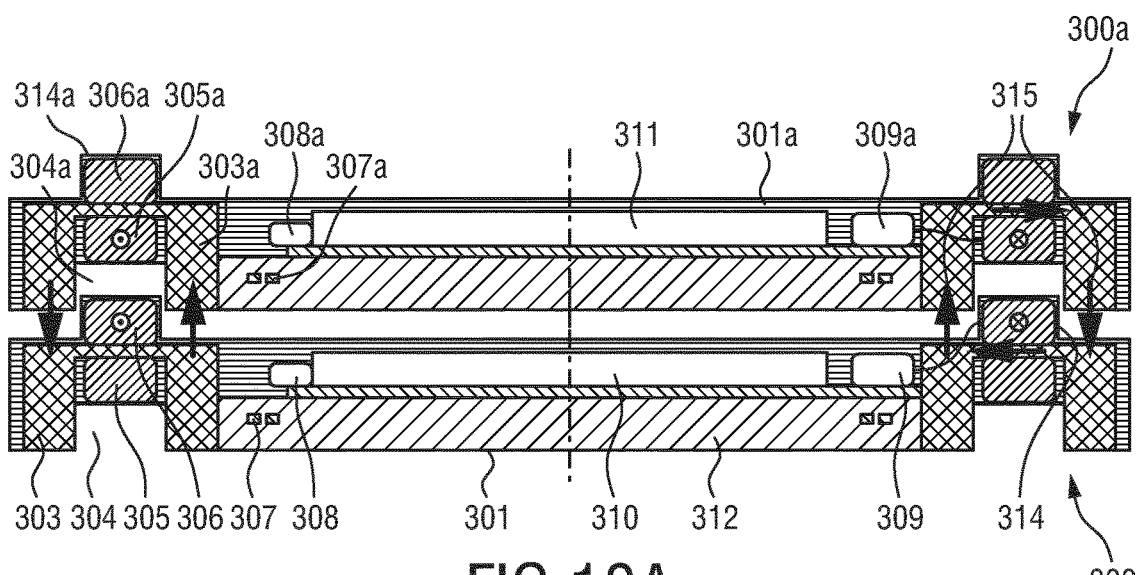
Figure 18B:
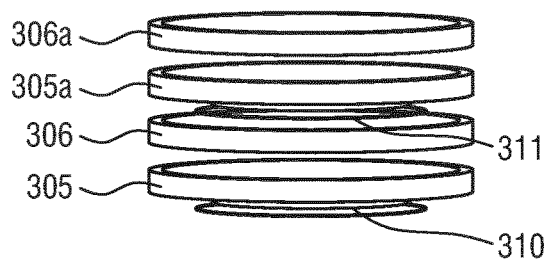
Figure 18C:
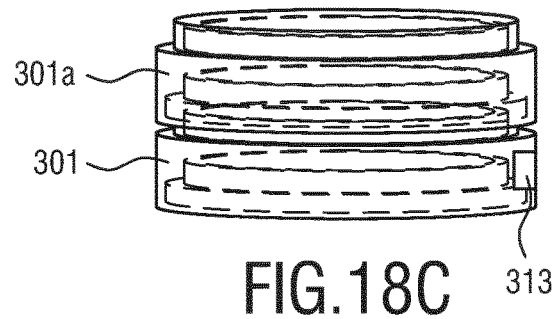

FIG. 17 schematically shows a first embodiment of a single stackable connector 300 for use in the system, wherein FIG. 17A shows a cross-sectional view, FIG. 17B shows a top view, FIG. 17C shows a first perspective view and FIG. 17D shows a second perspective view. FIG. 18 schematically shows two stackable connectors 300, 300a of the kind as shown in FIG. 17 stacked upon each other, wherein FIG. 18A shows a cross-sectional view, FIG. 18B shows a first perspective view and FIG. 18C shows a second perspective view. The connector 300 comprises a housing 301 and a magnetic coupling unit 302 arranged within the housing 301 for transmitting power to and/or receiving power from another device of the system having a counterpart connector by use of inductive coupling. Said magnetic coupling unit 302 includes a flux concentrator 303 (preferably being rotational symmetrical, e.g. ring-shaped, and made of high-permeable material), at least part of which having a U-shaped (or C-shaped) cross-section forming a recess 304 between the legs of the U. A first coil 305 is arranged within a recess 304 of the flux concentrator 303. A second coil 306 is arranged opposite the first coil 305 and outside of the recess 304 in which the first coil 305 is arranged. The flux concentrator 303 may one of different possible forms, such as a ring-shaped form, a circular symmetrical form, the form of a square, triangle, rectangle, etc.

Further, a ring-shaped RF antenna 307 (as part of a data transmission unit) arranged inside of the flux concentrator, an RF unit 308 (comprising radio electronics), a power unit 309 (such as magnetic power electronics) and a measurement unit 310 may be provided in or on the PCB 312. In the second connector 300a a battery 311 is provided instead of the measurement unit 310. Further, a PSC unit 313 may be provided in the connector, as shown in FIG. 18C, for coupling with a sensor. The outer surface of the housing is preferably fully covered by isolated material (e.g. a plastic material) for galvanic isolation, watertight sealing and mechanical stability.

The housing 301 is arranged to allow stacking of two or more of such connectors 300, 300a upon each other as e.g. shown in FIG. 18 so that the second coil 306 of the connector 300 and the first coil 305a of the second connector 300a (or vice versa, depending on the sequence in which the connectors 300, 300a are stacked upon each other) stacked upon the connector 300 together form a first transformer for inductive power transmission there between.

A circular bulge 314, 314a formed on the top surface of the connectors fits into the circular recess 304, 304a on the bottom of the next connector. The upper coil 306 of the connector 300 together with the lower coil 305a of the connector 300a is thus enclosed by high-permeable magnetic material of the flux concentrators 303, 303a. As a result said coils are now intimately coupled, which enables efficient power transfer. The arrows 315 show the magnetic flux lines when said coils are actuated as indicated. In this way stray flux is minimized which avoids crosstalk to/from the measurements and the radio signals. If needed conductive sheet material can be added to short-circuit any remaining flux components.

All the components of the connector 300, 300a including measurement unit, battery, cable connector (PSC unit) are preferably fitted into circular shaped sealed box 301, 301a representing the housing. Due to the rotational symmetric design, no particular positioning of two connectors in radial direction is required for stacking, but in this way connectors can be easily stacked on top of each other. Beside the circular shape other shapes are possible, e.g. with reduced rotational angle, square shape, shapes with extension in four directions, etc.

Preferably, the pole-tips of the inverted U core are not covered with (thick) plastic, because this will negatively affect the efficiency and introduce stray flux. Isolation can be guaranteed by reducing the plastic thickness, e.g. to a few tenth of a mm. Alternatively, galvanic isolation can be guaranteed though, because (composite) ferrite material may have a high intrinsic resistivity and internally the coils and the magnetic core can be isolated.

The transfer of magnetic power does preferably not start before a large coupling between coils and RF is detected, as explained above with respect to FIGS. 10 to 16. In the example shown in FIG. 18 only the lower coil 305a and the upper coil 306 are used, the other coils are not actuated at all.

For reasons of efficient power transfer and high radio SNR, the coupling areas should be large enough. Therefore, preferably, coils 305, 306, 305a, 305b and RF antennas 307, 307a are located on the outer area of the respective connector 300, 300a.

The PSC unit 313 for connecting one or more sensors to the connector 300 comprising a measurement unit 310 is preferably located on the side of the connector 300 in order to have full freedom of stacking. But the PSC unit 313 may also be located e.g. on the upper part of the connector 300 when restricted to have always a connector 300 including a measurement unit 310 on top of the stack.

Figure 19:
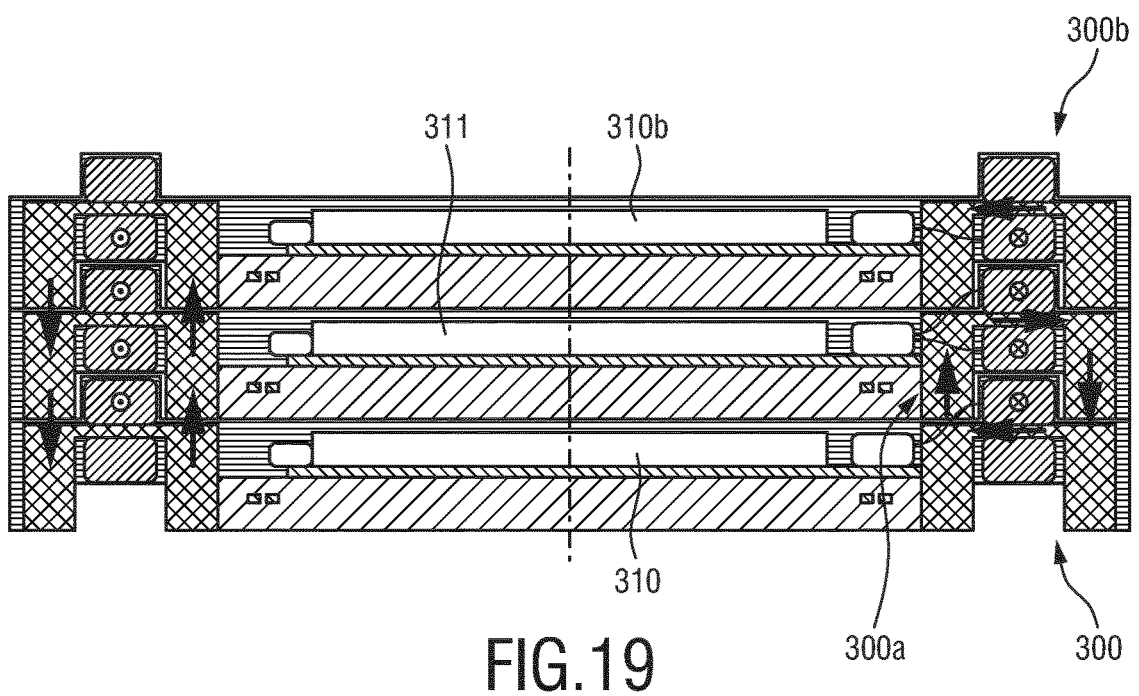

FIG. 19 shows three connectors 300, 300a, 300b stacked upon each other, wherein the connectors 300, 300b are identical and configured as shown in FIG. 17 and each comprise a measurement unit 310, 310a, whereas the connector 300a is configured as shown in FIG. 18 and comprises a battery 311. The measurement units 310, 310b are thus fed by the same battery 311 of the connector 300a (hereby, the battery 311 may also be located at a different position, e.g. at the bottom or top position). In this case, both coils 305a, 306a of the connector 300a are used to supply energy to the measurement units 310, 310b. Many variations on this scheme are possible, e.g. receiving power from one connector via one coil and at the same time supplying power to another connector via another coil.

The present invention is applicable for virtual any combination of stacked connectors including in any kind of device used in a system as e.g. shown in FIG. 2, e.g. in a patient monitoring system. Hence, one or more measurement modules, battery units, cable units and processing units may be easily coupled for cordless transfer of power and/or data. It enables even chaining devices to each other. A daisy chain is e.g. valuable in body worn sensing to avoid cable cluttering by connecting devices (e.g. measurement module) via one single connection or cable (comprising connectors) to a patient monitor, a powering device or a hub. This concept is illustrated in FIG. 20 showing the arrangement of several devices in the form of a daisy chain, each device including one or more of the connectors.

Figure 20A:
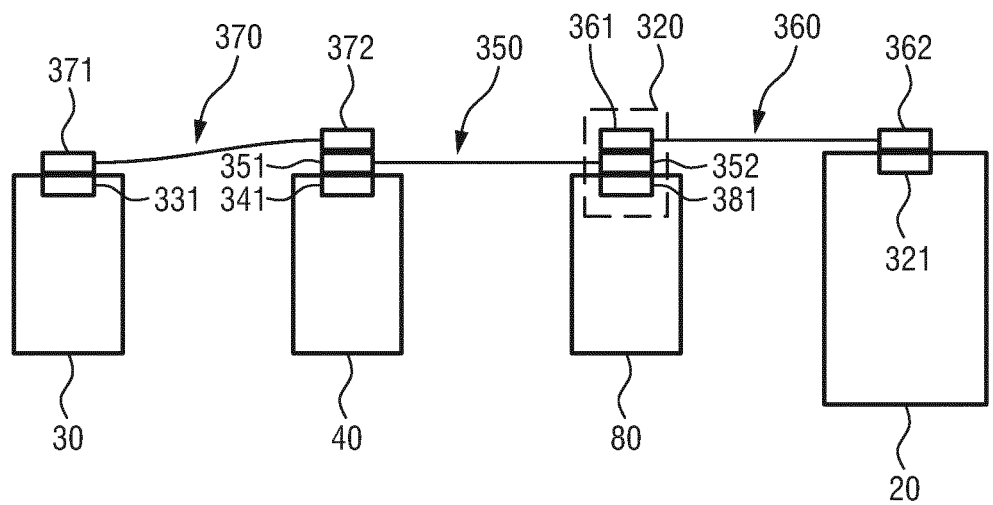
Figure 20B:
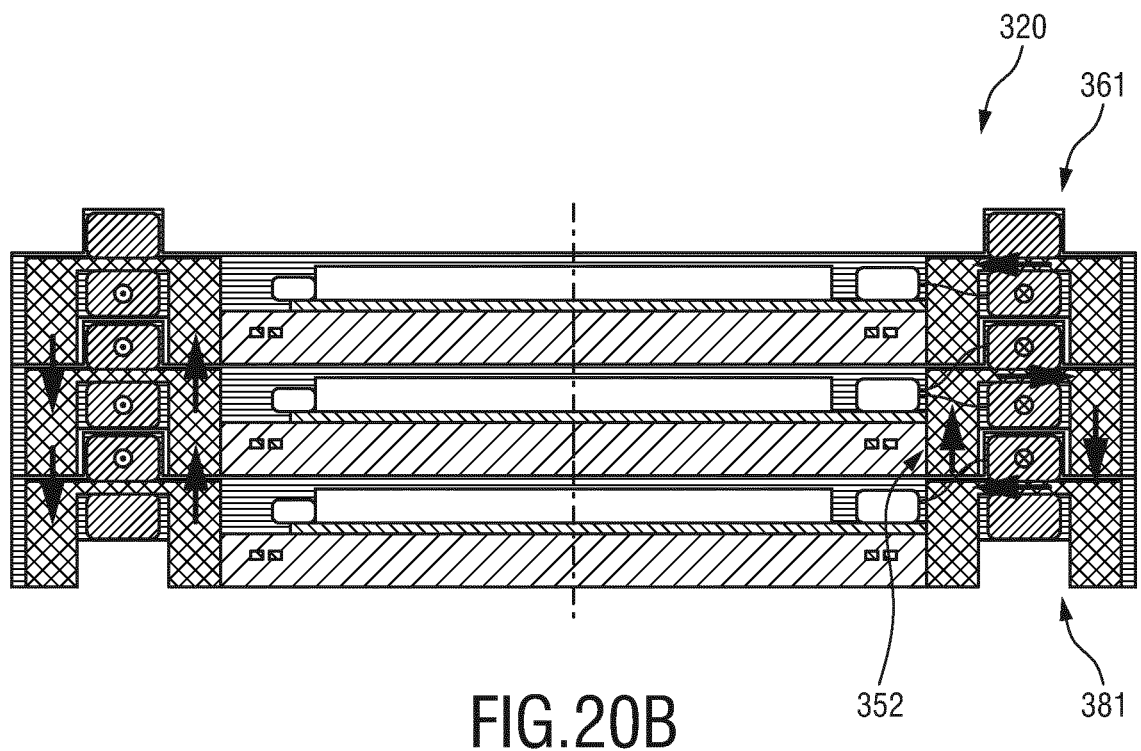

FIG. 20A shows a serial coupling of three measurement modules 30, 40, 80 (e.g. of the kind as shown in FIG. 2) coupled in series and coupled to a central processing unit 20 (e.g. of the kind as shown in FIG. 2). FIG. 20B shows a cross-sectional view of a stack 320 of three connectors 381, 352, 361 of the kind as shown in FIG. 17, wherein connector 381 is part of measurement module 80, connector 351 is part of a first cable unit 350 and connector 361 is part of a second cable unit 360. The first cable unit 350 comprises, at each of its ends, a connector 351, 352 and connects the measurement module 80 with the measurement module 40 having a connector 341 of the same kind. The second cable unit 360 comprises, at each of its ends, a connector 361, 362 and connects the measurement module 80 with the central processing unit 20 having a connector 321 of the same kind. A third cable unit 370 comprises, at each of its ends, a connector 371, 372 and connects the measurement module 40 with the measurement module 30 having a connector 331 of the same kind.

Hence, in this example, the measurement module 80 is connected to two cable units 350, 360. The cable unit 360 thus can transport power and data for the complex of the three measurement modules 30, 40, 80 to and/or from the central processing unit 20. Data and power may be relayed, transferred and/or exchanged between the stacked connectors. Power transfer may be performed by using additional rectifier and transmit electronics (e.g. DC/AC conversion), or by simply sharing AC current between coils, which is the most efficient option in terms of hardware.

It should be noted that the arrangement of the other stacks of connectors shown in FIG. 20A, e.g. of connectors 321 and 362 or of connectors 341, 351 and 372, is similar or identical as the arrangement of the stack 320 shown in FIG. 20B.

Figure 20C:
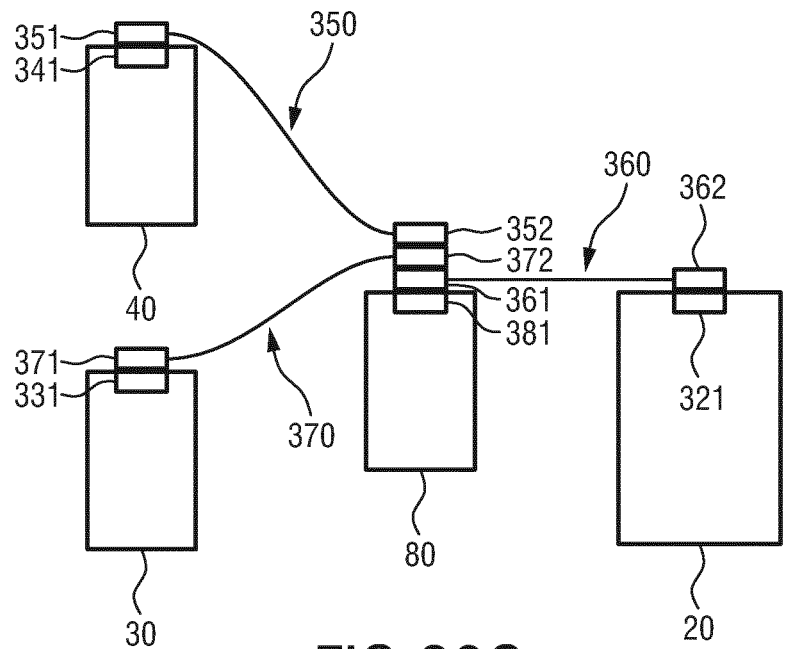

According to the same principle a star configuration is possible as shown in FIG. 20C instead of the series configuration shown in FIG. 20A.

It should be noted that combined power and data transport via the same cable is preferred, but alternatively any combination of short range radio cable and local batteries is also feasible.

Figure 21A:
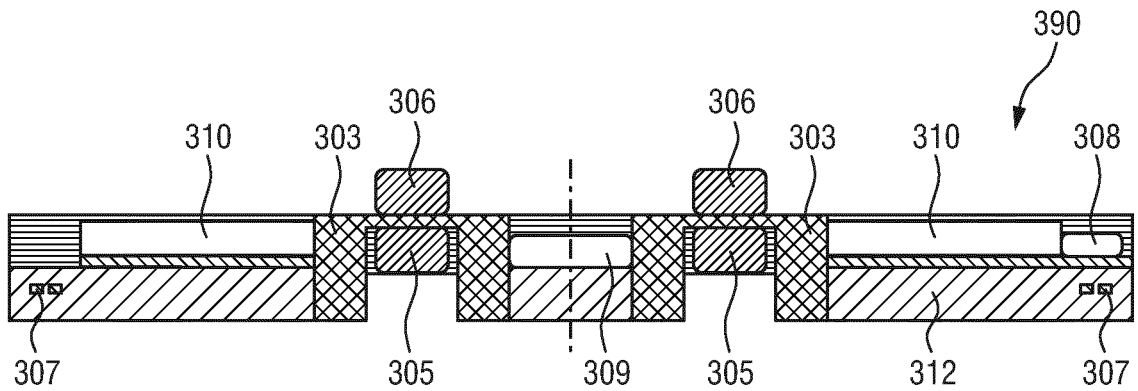
Figure 21B:
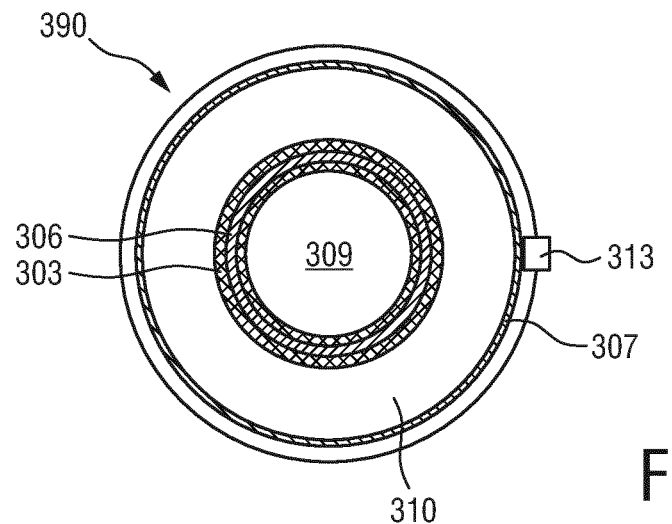
Figure 22A:
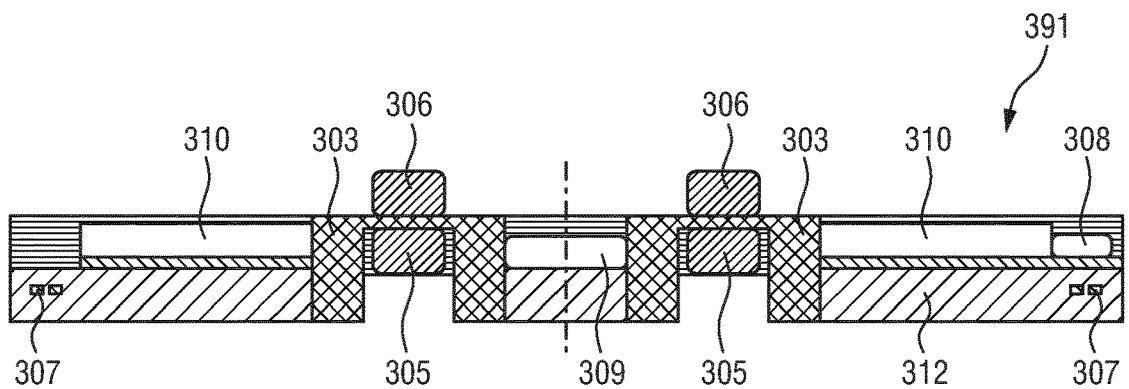
Figure 22B:
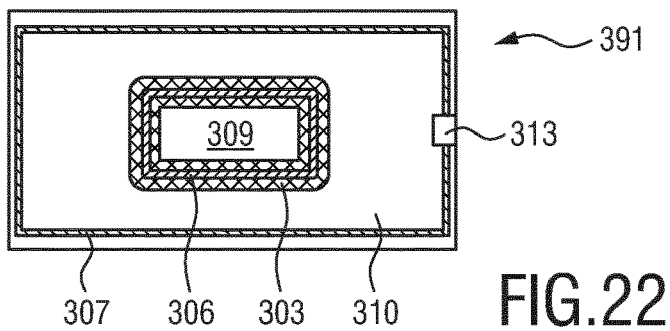
Figure 23A:
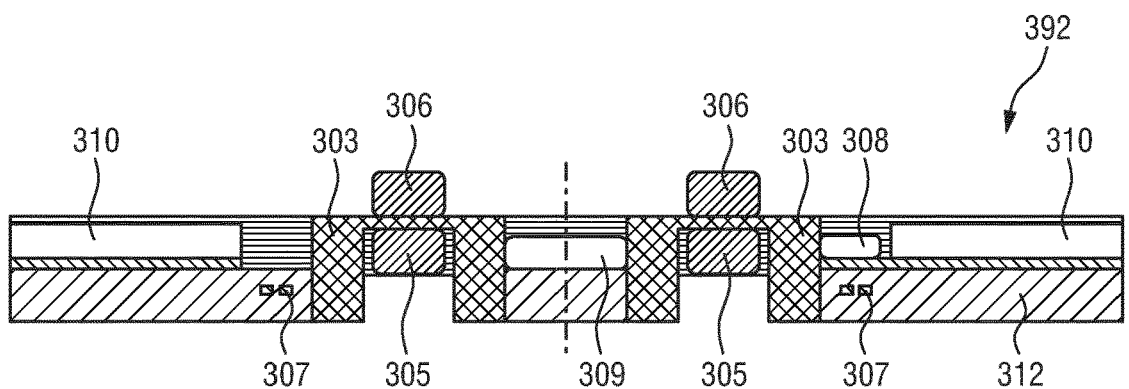
Figure 23B:
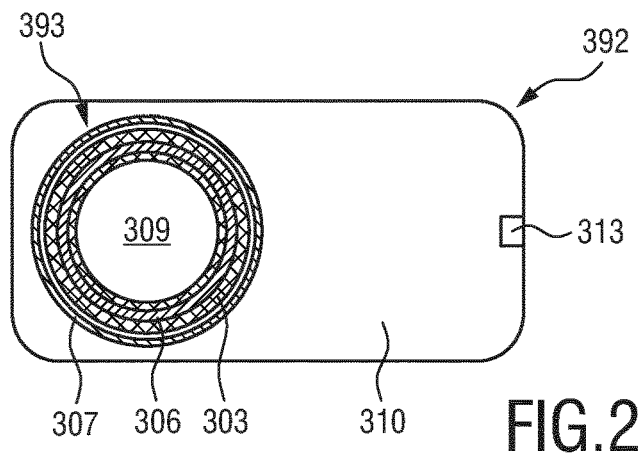
Figure 23C:
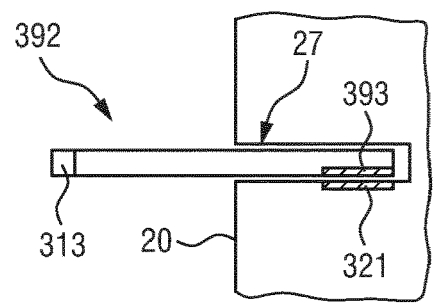

FIGS. 21 to 23 show further embodiments of a stackable connector having an alternative connector geometry compared to the connector geometry shown in FIG. 17. FIG. 21A shows a cross-sectional view of a circular connector 390, in which the area outside the flux generator 303 is occupied by measurement electronics 310 and/or a battery. FIG. 21B shows a top view of said connector 390. FIG. 22A shows a cross-sectional view and FIG. 22B shows a top view of a rectangular connector 391. FIG. 23 shows a smartcard sized connector 392 in a cross-sectional view (FIG. 23A), a top view (FIG. 23B) and a simplified cross-sectional view (FIG. 23C), which can be sandwiched between the walls of a patient monitor slot 27. Via coupling units 321, 393 the central processing unit 20 and the connector 392 are coupled.

Figure 24:
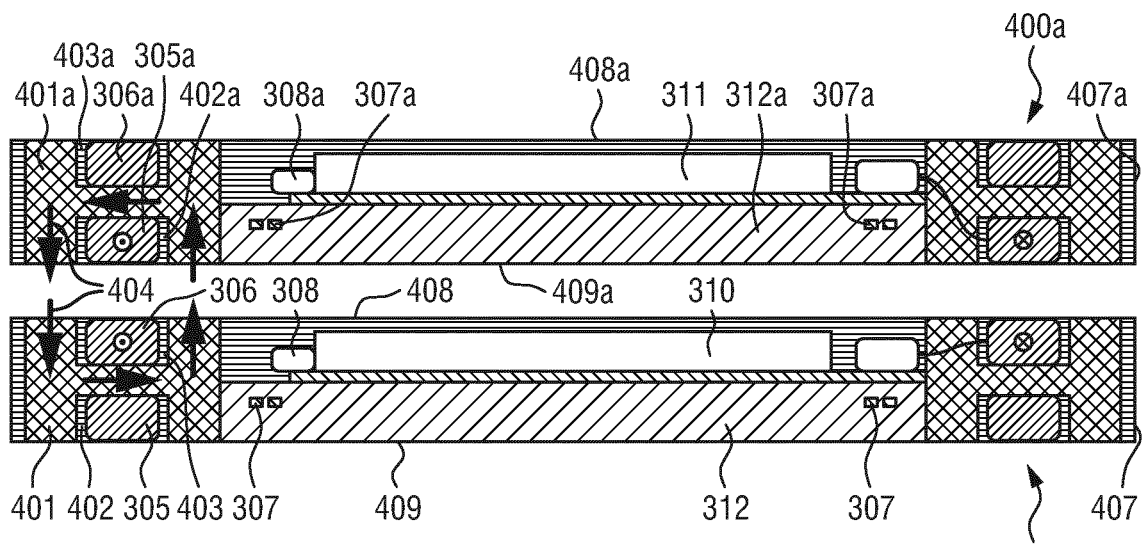

In an embodiment the upper and/or lower surfaces of the connector is totally flat. This makes e.g. cleaning easier. Corresponding embodiments of a connector 400, 410 are shown in FIGS. 24 and 25. There are further embodiments possible with other alignment structures or features to ensure exact positioning and tight alignment (preferably <1 mm) between the flux concentrators of different connectors when stacked together. For instance, the gap (having a low μ) between flux concentrators (having a high μ; including plastic insulation of housing) should be <0.5 mm+/−0.1 mm in a particular application. Lateral displacement should be small compared to geometry of poles (e.g. <0.5 mm).

FIG. 24 shows a cross-sectional view of a connector 400 (including a measurement module 310), 400a (including a battery 311) having a housing 407, 407a with flat main surfaces 408, 409, 408a, 409a using a flux concentrator 401, 401a having a cross section in the form of an H. Each flux concentrator 401, 401a comprises a first (lower) recess 402, 402a, in which the first (lower) coils 305, 305a are arranged, and a second (upper) recess 403, 403a, in which the second (upper) coils 306, 306a are arranged The lower coil 305a of the connector 400a and the upper coil 306 of the connector 300 together the lower part of the flux concentrator 401a and the upper part of the flux concentrator 401 form a transformer, as indicated by the arrows 404.

Figure 25A:
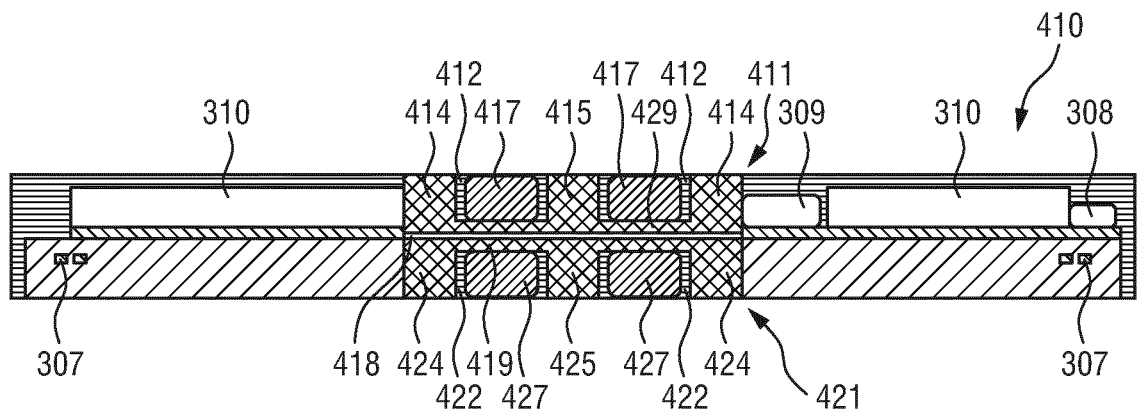
Figure 25B:
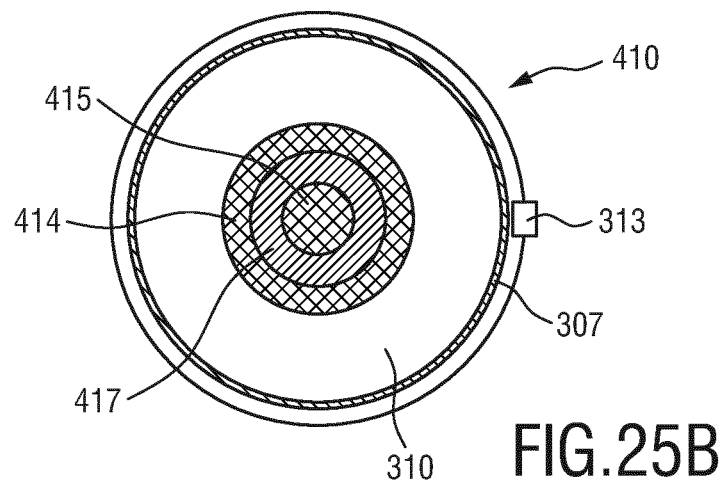

FIG. 25A shows a cross-sectional view of a connector 410 (including a measurement unit 310) having flat surfaces. A top view of the connector is shown in FIG. 25B. The connector 410 comprises two flux concentrators 411, 421, each having a U-shaped cross-section and each forming a recess 412 and 422, wherein each recess is formed between two neighboring legs 414, 415 and 424, 425 of the respective U, i.e. between the respective outer ring 414, 424 and the respective inner ring 415, 425 (which is a central finger in this embodiment). A first coil 417 is arranged within the recess 412 of the first flux concentrator 411 and a second coil 427 is arranged within the recess 422 of the second flux concentrator 421.

The two flux concentrators 411, 421 may also be seen as a common H-shaped flux concentrator, in which the two legs 414, 415, 424, 425 of the H-shaped flux concentrator 421 are arranged adjacent to each other or formed integrally and in which the transverse joint between the legs of the H is split into two joint elements 419, 429 with a shielding 418 arranged there between and perpendicular to the legs 414, 415, 424, 425 of the H.

Figure 26A:
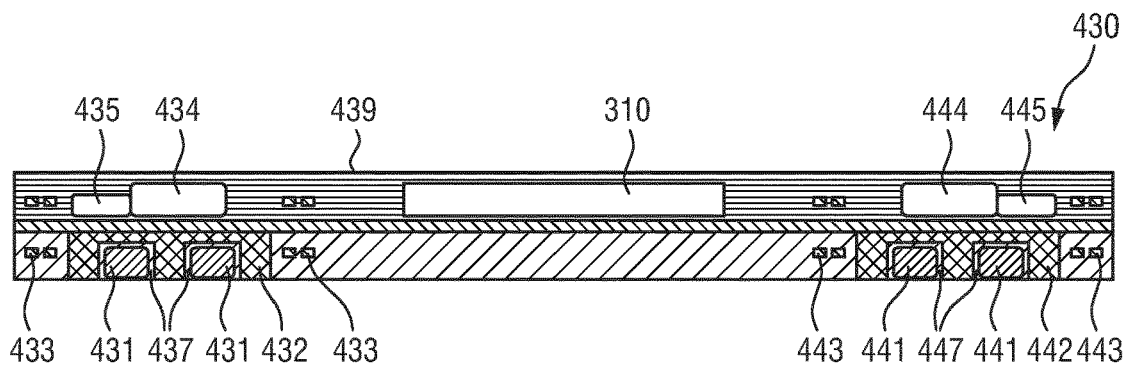
Figure 26B:
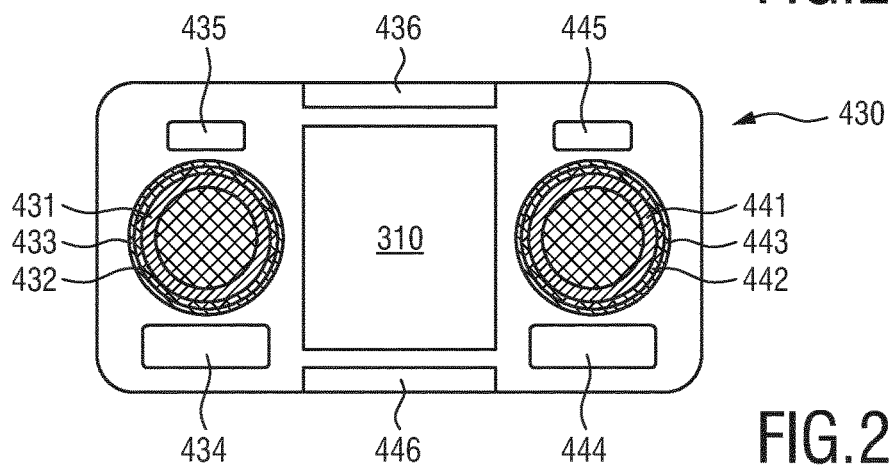

The concept of stacking can also be converted to a lateral geometry. This is beneficial to reduce building height. A cross-sectional view of an embodiment of a connector 430 having a lateral geometry is shown in FIG. 26A and a top view of the connector 430 is shown in FIG. 26B. The connector 430 comprises, separately at its left side and at its right side, coils 431, 441 arranged in the recess 437, 447 of a respective flux concentrator 432, 442 (each having an U-shaped cross-section like the flux concentrators 411, 421 shown in FIG. 25A). Around the flux concentrators 432, 442 ring-shaped RF antennas 433, 443 are arranged. Further, two power units 434, 444, two RF units 435, 445 two PSC units 436, 446 and a measurement unit 310 are provided. The flux concentrators 432, 442 are thus arranged laterally displaced with respect to each other, so that the first flux concentrator 432 and the second flux concentrator 442 are arranged at opposite areas and adjacent to the same surface of the housing. The housing 439 is preferably flat or has flat surfaces.

Figure 27A:
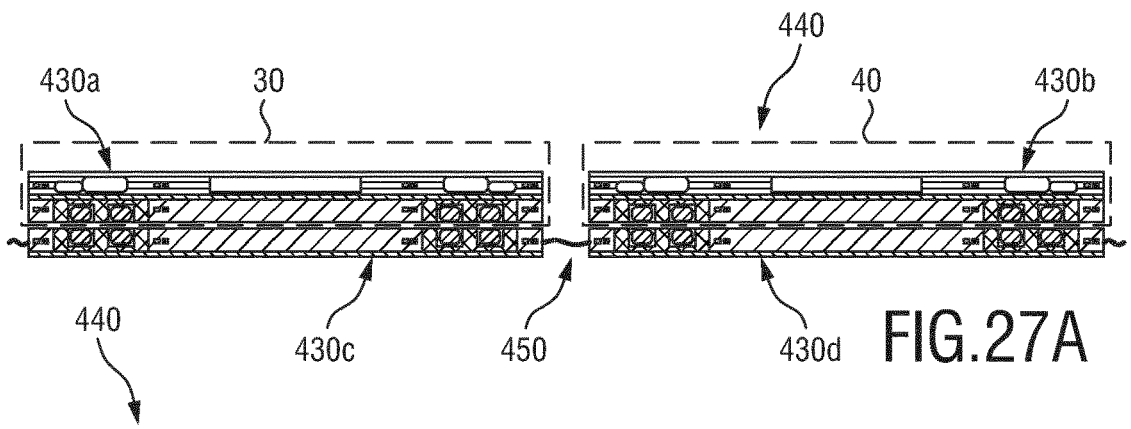
Figure 27B:
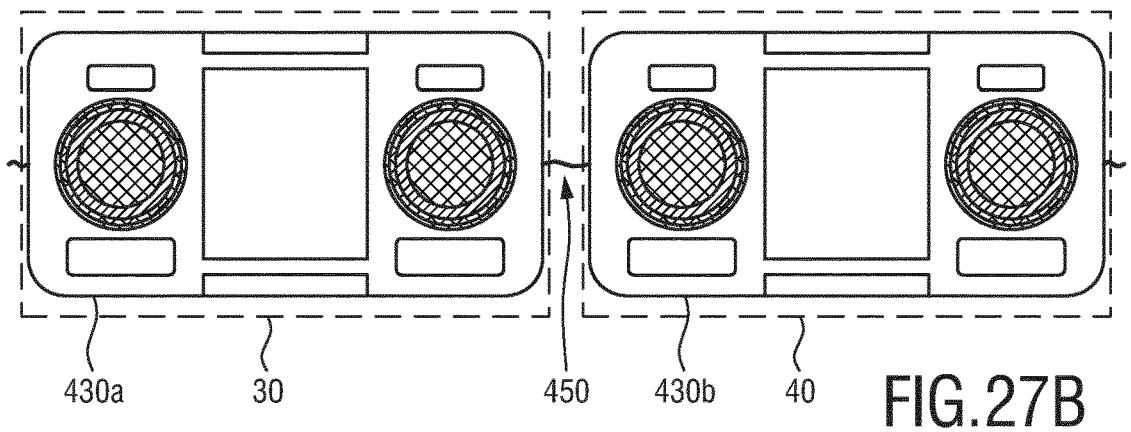

FIG. 27 shows a daisy chain 440 formed between measurement modules 30, 40, each comprising a connector 430a, 430b as shown in FIG. 26, by use of a cable unit 450 comprising connectors 430c, 430d as shown in FIG. 26. FIG. 27A shows a cross-sectional view of the daisy chain, FIG. 27B shows a top view. Such a cable unit 450 may comprise two or more of such connectors, preferably one at each end, but optionally additional connectors in between the ends.

Figure 28A:
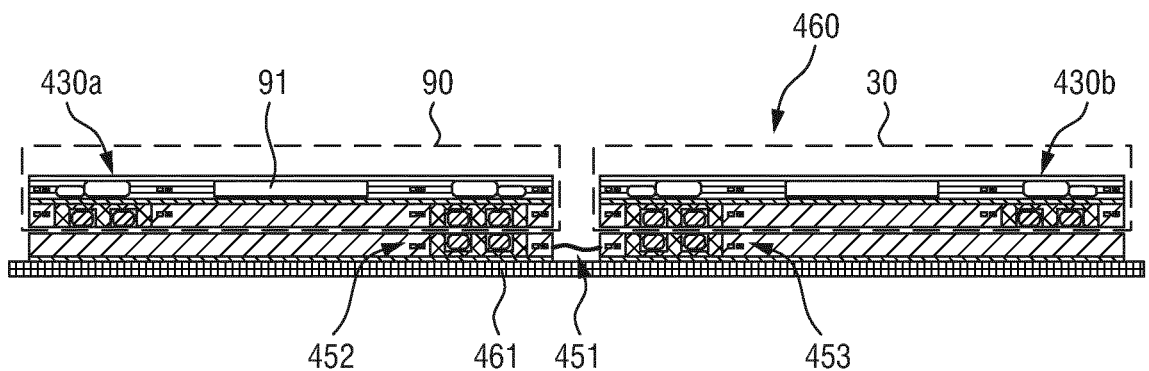
Figure 28B:
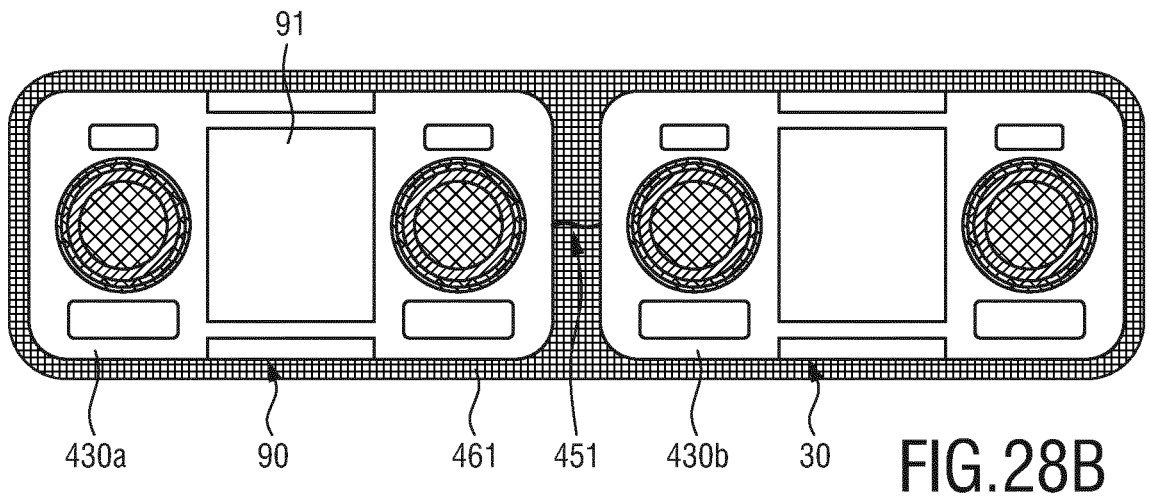

FIG. 28 shows a body worn sensor arrangement 460 in a cross-sectional view (FIG. 28A) and a top view (FIG. 28B). The body worn sensor arrangement 460 comprises a stackable support layer 461 carrying a cable unit 451, similar or identical to the cable unit 450 shown in FIG. 27, comprising connectors 452, 453, like the connectors 430c, 430d or with just a single coupling unit as shown in FIG. 28A. On said cable unit one or more measurement modules 30 and/or a battery module 90 (comprising a battery), each comprising a connector 430a, 430b, may be arranged.

Figure 29:
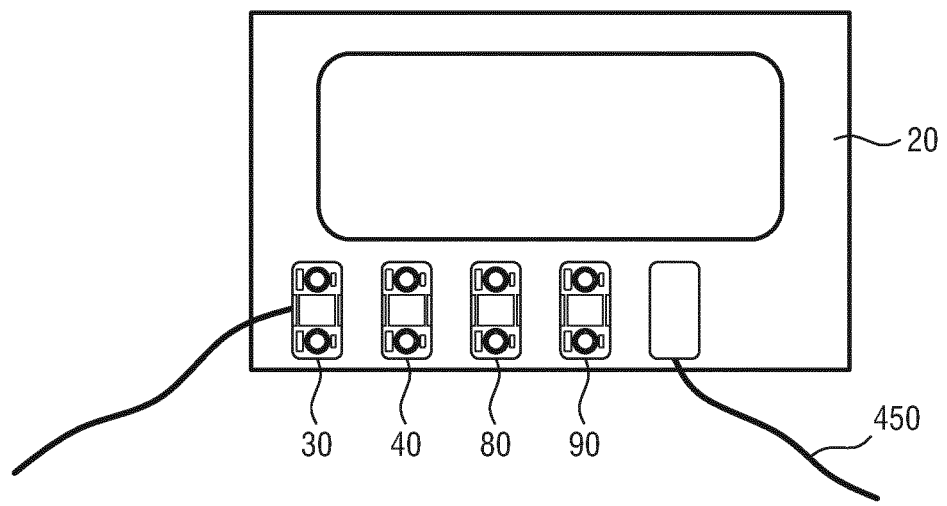

Measurement modules 30, 40, 80, battery modules 90 and cable units 450 can also be connected to e.g. a patient monitor or a central processing unit 20 using the same lateral geometry concept as schematically shown in FIG. 29. Further, any combination of vertical stacking and lateral connection is generally possible with the connectors as proposed by the present invention. For instance, a measurement module may have both vertical stacking and lateral stacking means.

In the following a battery module comprising a connector will be described in more detail.

Figure 30:
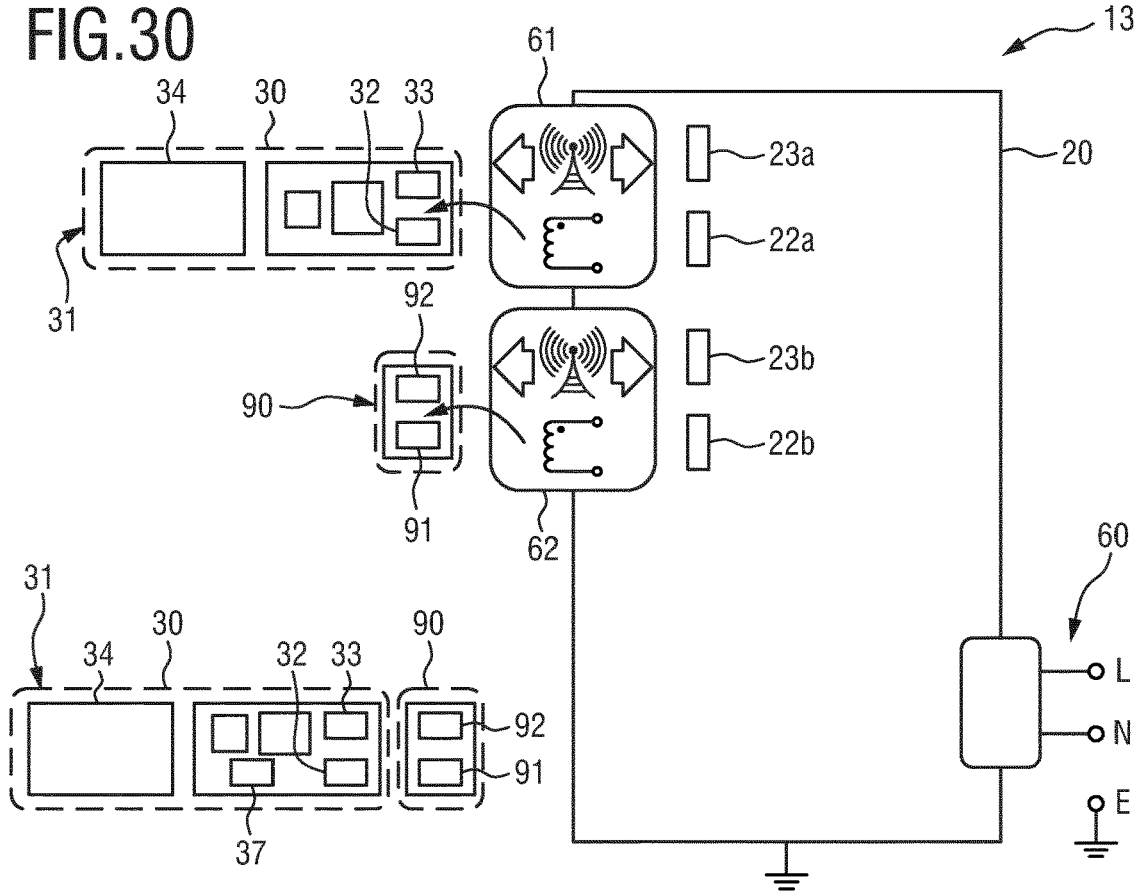
FIG. 30 shows a schematic diagram of a fourth embodiment of a system comprising a battery module.

As described above, plug-in measurement modules are coupled to the central processing unit via the proposed connector using magnetic powering and RF data communication. In addition, via its RF channel a battery (or any other energy storage element) may be made part of the network, e.g. a patient network, and may be coupled to other devices, such as measurement modules and the central processing unit in the same manner. This is schematically illustrated in FIG. 30 showing a schematic diagram of another embodiment of a system 13 including a measurement module 30, a central processing unit 20 and a battery module 90.

In a wireless measurement scenario the bi-directional battery module 90 may be snapped onto the measurement module 30 to supply energy magnetically via the proposed connector. Optionally, the measurement module 30 itself may comprise a small buffer battery 37 (or any other energy storage element) for temporarily bridging the transition time between wired and wireless scenarios.

The battery module 90 preferably comprises a battery 91 (also called battery unit) and a coupling unit 92 for magnetic power transmission between the battery module and other devices, e.g. to load the battery when the battery module 90 is coupled to the central processing unit 20 and to load the battery 37 of the measurement module 30 when the battery module is coupled to the measurement module 30. Optionally, means for data transmission may be provided in the battery module 90 as well.

Figure 35:
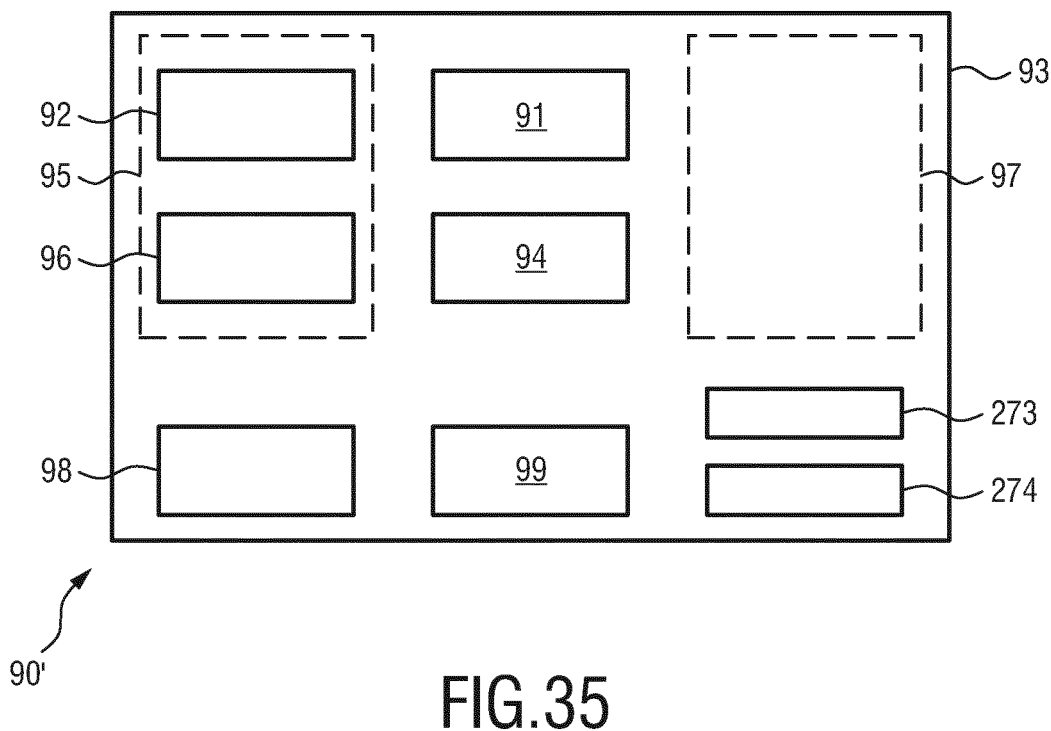
FIG. 35 shows a schematic diagram of an embodiment of a battery module.

A more detailed schematic diagram of a battery module 90' for wireless exchange of data and power between the battery module and another device of a system, in particular of a patient monitoring system, to which said battery module is coupled, is shown in FIG. 35. Said battery module 90' comprises a sealed housing 93, a battery unit 91 for storing electrical energy, a data storage unit 94 for storing data, and a connector 95. The connector comprises a data transmission unit 96 for transmitting data to and/or receiving data from another device of the system having a counterpart connector and a magnetic coupling unit 92 for transmitting power to and/or receiving power from another device of the system having a counterpart connector by use of inductive coupling.

Optionally, a second connector 97 is provided for simultaneously transmitting data to and/or receiving data from two other devices of the system and/or for simultaneously transmitting power to and/or receiving power from two other devices of the system.

The connector and its elements may be configured as explained above with respect to other devices and other embodiments. This holds particularly for the magnetic coupling unit 92 and for the data transmission unit 96, which may be configured as disclosed herein, e.g. as shown in any one of FIGS. 10 to 15 or 17 to 28.

The battery 91 may e.g. be a rechargeable battery, disposable battery or a super-capacitor and may be fitted into a smooth sealed plastic box, well protected for mechanical damage and fluids. It can be physically attached (i.e. put in close contact) to another device having a proposed connector (e.g. measurement module, cable unit or patient monitor), e.g. via an easy to use snap on or slide-In mechanism. Permanent magnets or alignment structures may be used to align and fixate its position for optimal power and radio transfer. When the battery 91 is empty, the battery module 90 can be attached (optionally via the cable) to any device in the system having a compatible connector and being able to charge, e.g. the patient monitor, a hub or a dedicated battery charger. Preferably, the same inductive/data connector topology is used throughout the whole architecture to couple all elements with each other. This enables that batteries can be charged anywhere providing a huge improvement on battery management.

Rechargeable battery life is almost always defined as number of full charge-discharge cycles by manufacturers and testers. In addition to cycling, the rate of degradation of lithium-ion batteries is strongly temperature-dependent; they degrade much faster if stored or used at higher temperatures e.g. when applied to the human body.

Therefore, the health and charge condition of the battery may be constantly determined from a temperature sensor, absolute time and the charge- and discharge profiles by using the voltage and/or current sensor(s), generally represented by sensor unit 98 in FIG. 35. On the basis of this information and historical data a self-diagnosis may be performed, which is communicated in the patient network to indicate the need for re-charging, for replacement or any faulty condition. Historical data may be stored locally (e.g. in the battery module) as well as shared in the network. Many scenarios are possible for this purpose.

The battery module 90' may further comprise a processing unit 99 for data processing of received data, time keeping, self-diagnosis and safety. Said processing unit may further be configured to calculate an expected operation time when applied to a measurement module 30.

Still further, the battery module 90' may, as illustrated in FIG. 16, comprise a detection unit 273 for detecting the strength of magnetic coupling between the magnetic coupling unit and a magnetic coupling unit of another device, and a control unit 274 for switching the data transmission unit into a low-power mode and/or for enabling the magnetic coupling unit, if the detected magnetic coupling is above a first threshold and/or its increase is above a second threshold, and for switching the data transmission unit into a high-power mode and/or for disabling the magnetic coupling unit, if the detected magnetic coupling is below a third threshold and/or its decrease is above a fourth threshold.

The main standards in wireless power transfer are the Qi standard and the Power Matters Technology (PowerMat) standard. Their main application is in the field of wireless charging. Qi comprises also a basic localization and recognizing mechanism for devices, low-power standby mode and power control.

An additional on-off switch using reed-contacts and a permanent magnet (e.g. the one present as part of the click-on fixation mechanism) may be useful as an extra layer of safety and battery leakage prevention, but there may also be other means for stacking detection, e.g. optical, capacitive or ultrasound means.

Li-ion and Li-polymer batteries are favorite candidates because of their high energy density per unit of mass and its large scale of use in the consumer domain. They have electronics means in place to watch its charge condition and protect from over-heating. Also the Qi standard has already some basic means in place to recognize valid loads. These may be used. These basic protection and monitoring means may be integrated into the complete architecture by combining magnetic and RF coupling as communication means, local intelligent safety monitoring and by connection to a patient network. For example, the absence of a valid identifier and/or the presence of a local failure condition may be a reason to abandon or not to start magnetic power transfer.

The charge status may be used to determine how long a battery can be applied for a particular measurement. This can be shown on e.g. the patient monitor display. Optionally, when attached to a measurement module, a visual or audio indicator on the battery itself may indicate when e.g. the available measurement time is less than 1 hour before replacement or charging should take place.

Integrating batteries in a medical setting as described above has serious consequences on safety, use case and workflow. Constraints include absolute safety, possible shape, less weight and size, easy replaceability/swappability by the nurse, easy cleanability, large capacity, and chargeability during wearing. Battery modules may be closed boxes, fully wirelessly connected for both charging as for supplying energy. The proposed architecture offers easily cleanable mechanical connections. Furthermore, they can be replaced within a few seconds while the measurement device stays in place.

In the following a cable unit comprising connector for connecting other devices of a network/system will be described in more detail.

Figure 31:
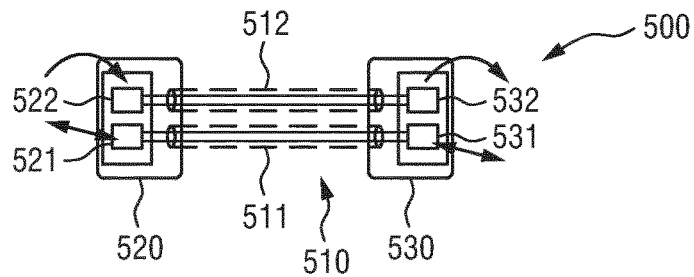
FIG. 31 shows a general layout of a cable unit.

A general layout of a cable unit 500 is shown in FIG. 31. The cable unit 500 comprises a cable 510 and a connector 520, 530 at each end of the cable 510. Each connector 520, 530 comprises a magnetic coupling unit 521, 531 and a data transmission unit 522, 532. The cable 510 comprises a first wire pair 511 (e.g. twisted wires) connecting the magnetic coupling units 521, 531 and a second wire pair 512 (e.g. twisted wires) connecting the data transmission units 522, 532.

Figure 32:
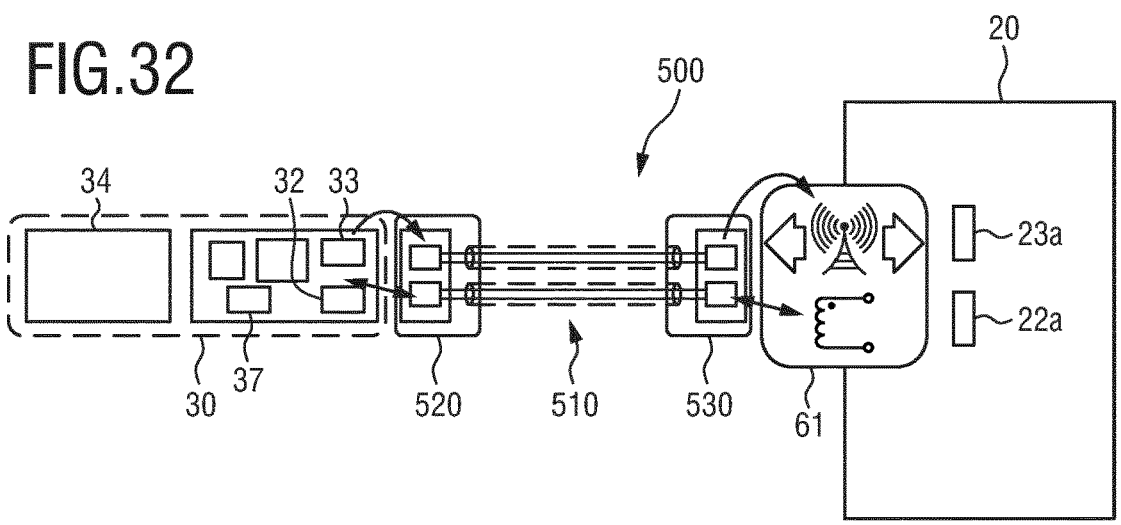
FIG. 32 illustrates the use of a cable unit in a high acuity setting.

FIG. 32 illustrates the use of a cable unit 500 in a high acuity setting, in this example for connecting a measurement module 30 and a central processing unit 20. Such a cable unit 500 may be used in an OR (operation room) or ICU (intensive care unit) setting to guarantee data integrity and power consistency for the measurement. The two wire pairs 511, 512 are preferably thin and flexible as used in catheter technology. Extra conductive shielding or ferrite common mode coils may be added for extra robustness and performance. This approach guarantees a sufficient high signal to noise ratio for the radio signal due to its low RF attenuation and shielding properties. Due to the large ratio between the frequencies for contactless powering (100-200 kHz) and the radio (2.4 GHz) the internal crosstalk is manageable.

Many options are possible for implementing the main functionality of this cable unit 500 to form a protected pipe for the radio- and power-signals.

One option is a fully passive cable unit comprising two wire pairs (as shown in FIGS. 31, 32). Basically RF data and power can be transferred in two directions across the cable unit. Twisted wires for power and a coaxial- or balanced transmission line for RF data may be used. Additionally, passive components may be added to the connector to further improve RF transmission by e.g. filtering and impedance matching, to improve (power) transfer by e.g. flux concentrators or for passive identification (optical tag).

Optionally, power and radio signals may be combined in one single wire pair (or coax cable). Attaching only one connector of the fully passive cable to e.g. a measurement module will neither increase the magnetic coupling nor the RF coupling. Two connections are made until pairing is initiated.

Another option is an active cable. Active components are present (in one or both connectors) to convert the magnetic power signals to clean/stabilized DC or sinusoidal AC before sending them across the cable. This limits crosstalk and disturbances from the power signal into the radio channel. The most logical location of said components is in the connectors(s), but they can also be distributed across (a part of) the cable unit, e.g. on a flexible foil integrated in the cable sleeve.

The data radio signal may be amplified, re-modulated (transponder), buffered or (actively) impedance converted to match the RF cable properties. Alternatively, conversion to another frequency band or to baseband may enhance signal integrity even more, for example by conversion to a serial bus format like e.g. USB, RS232 or TCP/IP. A part of the magnetic power is used to power said active components.

Each connector may be arranged and act in itself as a node and be a part of the patient network, including unique identifier, radio and network stack for pairing as well as magnetic powering. Additional radios may be added to relay radio signals (e.g. in a daisy chain) or to implement separate channels for patient network management. Active cables may transport data or power in only one direction; hence, more wire pairs per cable or more cables may be needed to transport in both directions.

According to another option conversion of the RF signal to the optical domain may be provided, which offers the ultimate level in data integrity and potentially also allows for a thinner cable.

Obviously, cables units may comprise solely power or data channels.

Identification tags (RFID) or a radio unit may be added to the cable unit or the connectors for identification and data management.

Preferably, from a user perspective, the cable unit should be able to transport RF data and power in two directions. This may need to use more wire pairs, e.g. in case when active components are applied.

Figure 33:
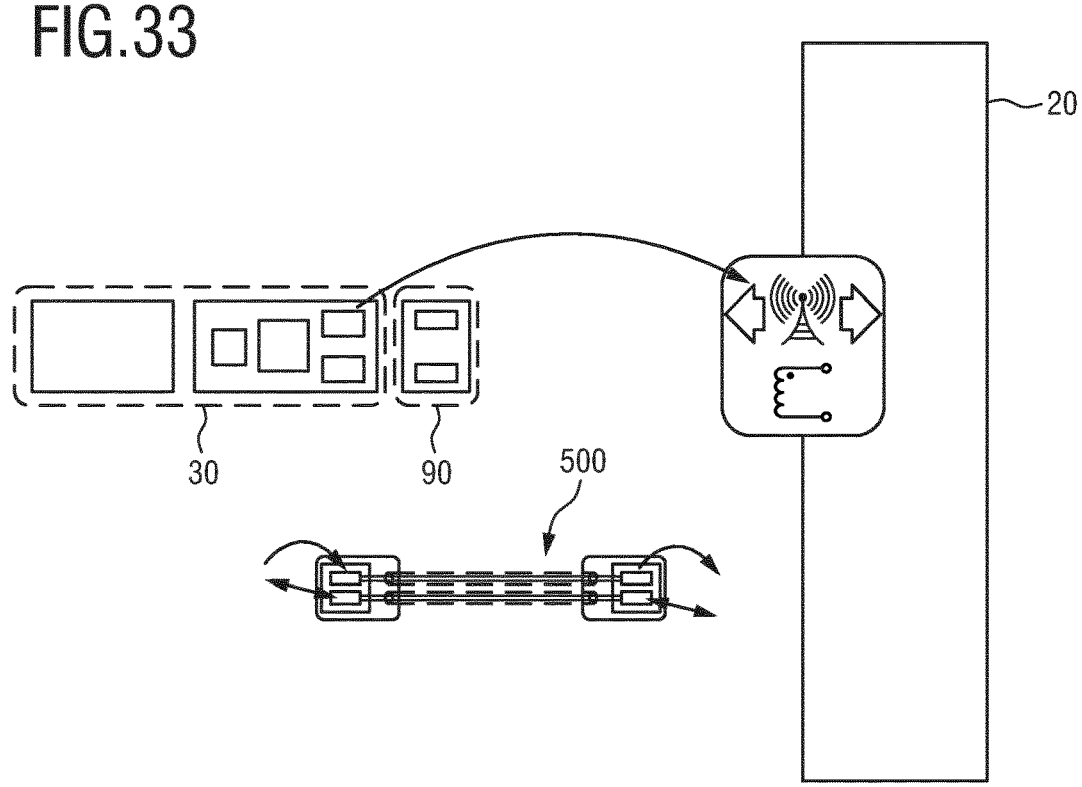
FIG. 33 illustrates the use of a cable unit in a lower acuity setting.

FIG. 33 illustrates the use of a cable unit 500 in a lower acuity setting, in this example for connecting a measurement module 30 (or battery module 90) and a central processing unit 20 only when needed for improving RF performance (e.g. in crowded areas), or for powering or charging reasons (i.e. saving battery capacity for mobile use). Measurement modules may be connected in a chain to avoid cable cluttering.

Figure 36:
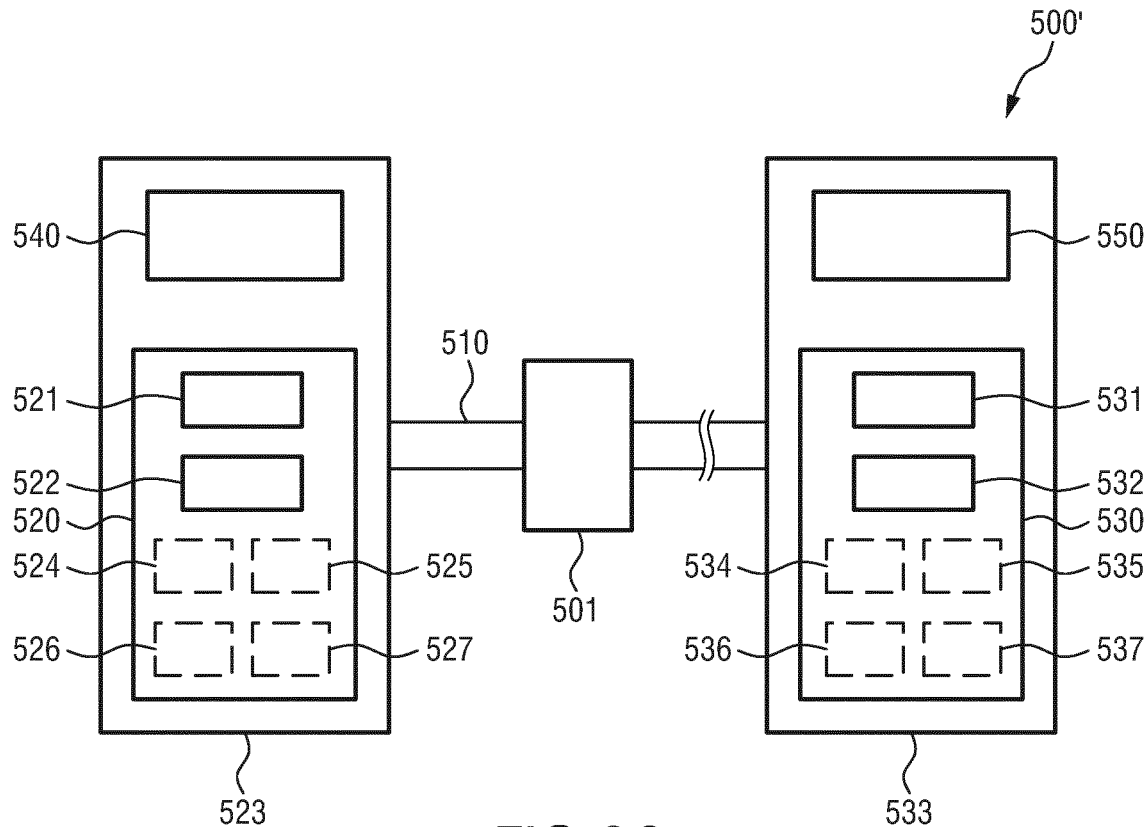
FIG. 36 shows a schematic diagram of an embodiment of a cable unit.

A more detailed schematic diagram of a cable unit 500' for connecting devices in a system, in particular in a patient monitoring system, to enable wireless exchange of data and/or power between them, is schematically shown in FIG. 36. As explained above, the cable unit 500' comprises a cable 510 and a connector 520, 530 arranged at each end of said cable. Each of said connectors comprises a data transmission unit 522, 532 for transmitting data to and/or receiving data from a device having a counterpart connector and a magnetic coupling unit 521, 531 for transmitting power to and/or receiving power from another device of the system having a counterpart connector by use of inductive coupling.

The cable unit 500' further comprises a (sealed) housing 523, 533 arranged at each end of the cable 510, in which the one or more connectors 520, 530 arranged at the respective end of the cable are arranged. The sealed housing is preferably configured as disclosed herein in the context of other devices to allow stacking of the cable unit 500' to other devices having a counterpart connector.

The connector and its elements may be configured as explained above with respect to other devices and other embodiments. This holds particularly for the magnetic coupling units 521, 531 and for the data transmission units 522, 532, which may be configured as disclosed herein, e.g. as shown in any one of FIGS. 10 to 15 or 17 to 28.

The cable unit 500' may further comprise electronic circuitry 501 for data processing, conversion and/or storage of received data.

Further, the cable unit 500', in particular each connector 520, 530, may, as illustrated in FIG. 16, comprise a detection unit 524, 534 for detecting the strength of magnetic coupling between the magnetic coupling unit (of the respective connector) and a magnetic coupling unit of another device, and a control unit 525, 535 for switching the data transmission unit (of the respective connector) into a low-power mode and/or for enabling the magnetic coupling unit (of the respective connector), if the detected magnetic coupling is above a first threshold and/or its increase is above a second threshold, and for switching the data transmission unit (of the respective connector) into a high-power mode and/or for disabling the magnetic coupling unit (of the respective connector), if the detected magnetic coupling is below a third threshold and/or its decrease is above a fourth threshold.

As an alternative option, the cable unit 500', in particular each connector 520, 530, may comprise a proximity detector 526, 536 for detecting proximity of the cable unit of another device (i.e. for detecting if there is only a small air gap in between) and a control unit 527, 537 for switching the respective data transmission unit 522, 532 (of the respective connector) into a low-power mode and/or for enabling the magnetic coupling unit (of the respective connector), if a device is detected to be proximate to the cable unit, and for switching the data transmission unit (of the respective connector) into a high-power mode and/or for disabling the magnetic coupling unit (of the respective connector), if no device is detected to be proximate to the cable unit. Such a proximity detector and control unit may also be used in other embodiments of the connector and in other devices disclosed herein.

Various methods of proximity detection may be used, e.g. received signal strength indication (RSSI) methods such as standard Bluetooth, Bluetooth Low Energy (BTLE) and Wi-Fi. Other example methods of proximity detection include differential methods such as ultra-wideband (UWB), optical methods using at e.g. infrared (IR) wavelengths ultrasound and NFC. Proximity detection methods such as IRDA, UWB and NFC typically use both standard and proprietary data transport mechanisms. In examples, proximity detection may occur when two devices are e.g. within a range of 0.5 mm+/−0.1 mm of each other, whereby other distances may be used.

Generally, direct or indirect means for detecting proximity of the device to another device may be used. The actual distance between two devices that can be detected as "proximate" depends e.g. on the magnetic design; one criterion may be if the magnetic coupling is larger than 90% or preferably larger than 95%, or ultimately larger than 99%. In an exemplary design a magnetic distance of ~0.5 mm+100 μm (due to 2*0.25 mm plastic housing) is used, which may be understood as "close proximity". However, other distances may be used instead, depending on the particular design and/or application.

Finally, within each housing 523, 533 a second connector 540, 550 may be arranged for simultaneously transmitting data to and/or receiving data from two devices and/or for simultaneously transmitting power to and/or receiving power from two devices. Said second connectors 540, 550 are generally configured in the same way as the first connectors 520, 530.

The proposed cable units may be used for mutually connecting measurement modules and monitoring devices. Daisy chains as well as star configurations, as shown in FIGS. 20A and 20C are possible. Cables units may be coupled laterally or vertically, on top of each other or with a third component in between. Alternatively, a distribution cable unit may have multiple branches to connect components physically.

In the following the pairing of devices will be explained.

A first option of pairing is to perform pairing manually, e.g. during the attachment of a measurement module to a person's body. By bringing a device physically in close proximity with another, identifiers are exchanged, which effectively means that said device is added into the network of devices, e.g. into the patient network. This is easy to achieve during first time attachment of the measurement module and for mobile patients.

The order of connecting is generally not important; every member of the network can communicate and update the network status, e.g. via a master device in particular standards, like Bluetooth-LE. Visual or audible information on the devices may indicate its connection status. It may e.g. indicate which devices are paired into a patient network, and it may indicate loss of RF connectivity to a hospital network or patient monitor of e.g. a mobile patient. In such a case the patient network needs to (automatically or manually) re-connect to another radio link.

The association mechanism starts when two conditions are met:
1. An increased level of magnetic coupling, which can be detected from the induced voltage in the secondary coil as well as the current in the primary coil or the resonance frequency of the assembly. When this condition is met, the RF radios start communicating with each other (could be via the master device).
2. When the strengths of the received RF signals are also above a pre-determined level, associating is started. Alternatively, deviating transmitter antenna impedance (voltage standing wave ratio VSWR, reflected waves) can be included as an extra check, indicating RF absorption of the transmitted signal.

Repeating this mechanism toggles the membership of a patient network, i.e. the master device knows all devices in the network of the specific patient; it switches between joining and leaving. Network membership may be shown by visual, tactile or audible actuators (e.g. LED, display, buzzer, beeper, vibrator, etc.). Additionally, a mechanical switch or keyboard code may be used to force leaving the network.

The patient may have plasters comprising patient-network functionality as extra identification- and localization means, to enforce that a measurement (or sensor) is attached on the correct position on the correct patient.

A second option of pairing is to connect immobilized (e.g. OR or ICU) patients to a patient network by use of a cable unit 500 as shown in FIG. 31. By connecting the cable unit between a measurement module and a monitoring device for a short time, the magnetic coupling and the RF amplitude will increase above a certain level, which triggers the pairing mechanism.

Figure 34:
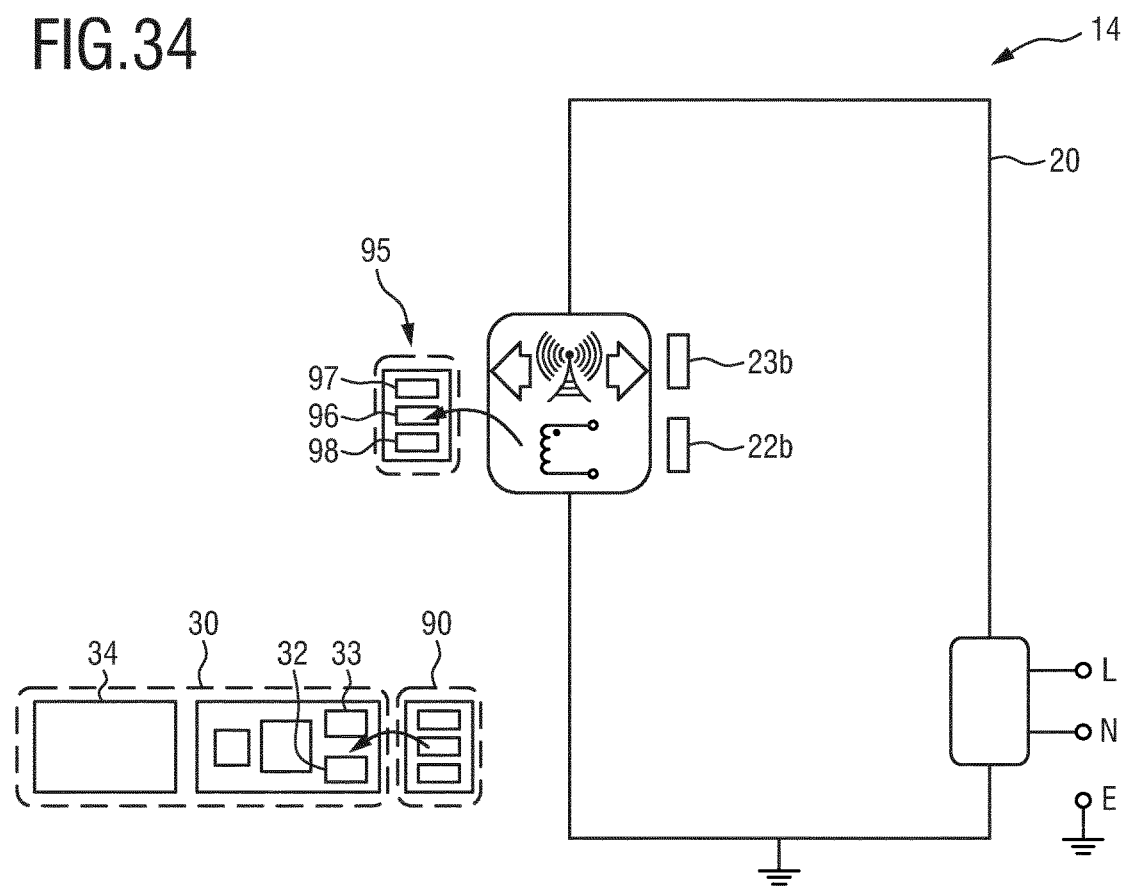
FIG. 34 shows a schematic diagram of a fifth embodiment of a system comprising a storage module.

A third option of pairing is to use a contactless storage module, which may be used as an intermediate storage container to transfer identifiers between components in the patient network. This is illustrated in FIG. 34 showing a schematic diagram of a fifth embodiment of a system 14 comprising a storage module 95. By bringing the contactless storage module 95 in close proximity of another component 20 or 30 having a counterpart connector the identifiers are interchanged and used to update the patient network. An additional mechanical push button or proximity detector may be used to trigger exchange. Preferably, only one identifier can be stored and transferred to avoid unambiguity.

The contactless storage module 95 can have the form-factor of a pencil, a smart-card or a small box like the measurement modules. Like other devices comprising a connector, it comprises, besides a storage element 98, a magnetic coupling unit 96 and a data transmission unit 97 (e.g. radio hardware) to couple to other devices having a counterpart connector.

A fourth option of pairing is to use additional trigger means. A push button or proximity detector (e.g. using optical, magnetic, ultrasound technology) may be added as a condition to initiate the pairing process. Additional trigger means are beneficial as an extra layer of robustness to omit components to detect the level of coupling (e.g. no RF or magnetic coupling measurement). Further, in case of a pencil-like device, the RF antenna and coil may be located in the tip; the maximum coupling may be below the predetermined threshold for triggering the association process.

Figure 37:
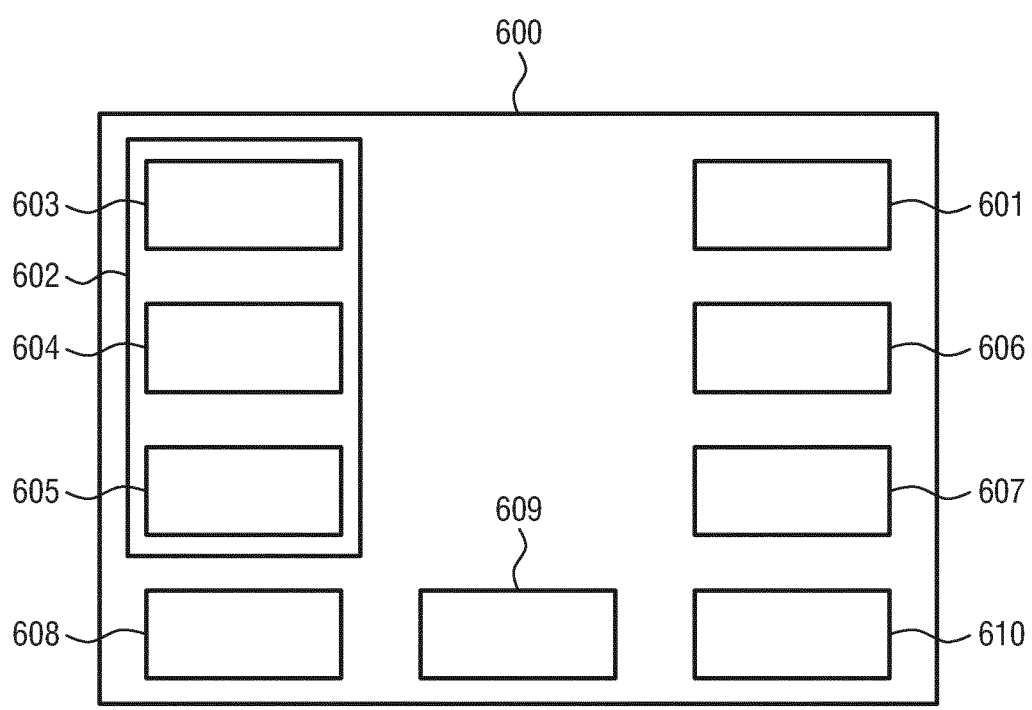
FIG. 37 shows a schematic diagram of another embodiment of a device applying a paring approach.

A more detailed schematic diagram of a device 600 for wireless transmission of data and/or power between the device and another device of a system, in particular of a patient monitoring system, is shown in FIG. 37. Said device 600 is configured to apply the above described approach for pairing and comprises an identification unit 601 for storing a unique identifier of the device and a connector 602. Said connector 602 comprises a data transmission unit 603 arranged for transmitting data to and/or receiving data from another device of the system having a counterpart connector, a magnetic coupling unit 604 for transmitting power to and/or receiving power from another device of the system having a counterpart connector by use of inductive coupling, and a detection unit 605 for detecting the strength of magnetic coupling between the magnetic coupling unit and a magnetic coupling unit of a counterpart connector of another device and for detecting the intensity of data received by the data transmission unit from a data transmission unit of the other device.

The device 600 further comprises a control unit 606 for controlling the data transmission unit 603 to transmit the unique identifier of the device to the other device and/or to receive the unique identifier of the other device, if a) the detected intensity of received data is above a data intensity threshold and/or its increase is above a data intensity increase threshold and b) the detected magnetic coupling is above a magnetic coupling threshold and/or its increase is above a magnetic coupling increase threshold.

The device 600 may further comprise a storage unit 607 for storing unique identifiers of other devices received by the data transmission unit.

The control unit 606 may be configured to control the data transmission unit to additionally transmit unique identifier of other devices stored in the storage unit and/or to receive unique identifier of other devices, if a) the detected intensity of received data is above a data intensity threshold and/or its increase is above a data intensity increase threshold and b) the detected magnetic coupling is above a magnetic coupling threshold and/or its increase is above a magnetic coupling increase threshold.

The detection unit 605 may be configured to detect impedance, resonance frequency and/or induced voltage for detecting the strength of magnetic coupling and/or to detect signal intensity and/or antenna impedance of an antenna of the data transmission unit for detecting the intensity of received data. The strength of magnetic coupling is often referred to as magnetic coupling factor k ($0<=k<=1$).

In case components are already connected, this is clear from the availability of power and strong RF signal. Attachment of a new component may be detected by use a polling mechanism to check the increase of magnetic coupling (and, optionally, an RF signal used for data transmission. Detection of disconnecting components may be performed by the inverse process: a polling mechanism to measure a decrease of the strength of magnetic coupling by use e.g. of impedance, resonance frequency and/or induced voltage (and, optionally, of the RF signal). Optionally, the RF signal strength may be measured in addition.

Generally, a first transmission of the unique identifier is interpreted as a request to couple the device with the system and a second transmission of the unique identifier is interpreted as a request to decouple the device from the system.

The device may further comprise an indicator 608, in particular a visual, tactile or audible indicator, for indicating the coupling status of the coupling of the device with the system.

Still further, the device may comprise a user interface 609 for enabling a user to initiate a transmission of the unique identifier or a coupling or decoupling request message.

Still further, the device may comprise a proximity detector 610 for detecting proximity of the device to the other device, wherein said control unit is control the data transmission unit the transmit the unique identifier of the device to the other device and/or to receive the unique identifier of the other device, if additionally proximity of the device to the other device is detected. The proximity detector may be configured as explained above with respect to other embodiments.

The connector 602 and its elements may be configured as explained above with respect to other devices and other embodiments. This holds particularly for the magnetic coupling unit 604 and for the data transmission unit 603 which may be configured as disclosed herein, e.g. as shown in any one of FIGS. 10 to 15 or 17 to 28.

Finally, the device 600 may further comprise a data unit 611 for generating and/or receiving data, and/or a power unit 612 for supplying and/or consuming power.

In the disclosed architecture it is foreseen to pass-through AC power from a power source (battery/cable) to stacked modules without any further processing (without re-modulation). The frequency of said power signal is thus always available in all modules and may serve as a master clock to derive timing pace locally. Additionally, the moment in time when modules (measurement modules, cable modules, battery modules) are stacked is a one-time trigger to (re)set the relative time between modules. Obviously, the radio channel may also be used to generate a one-time trigger signal. This concept will be further described in the following.

Figure 38A:
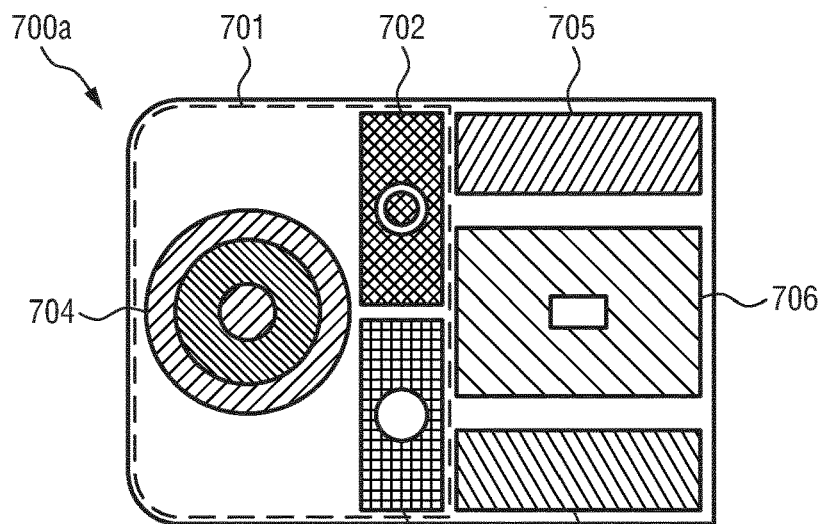
FIGS. 38A and 38B show different views of a first embodiment of a device according to the present invention.
Figure 38B:
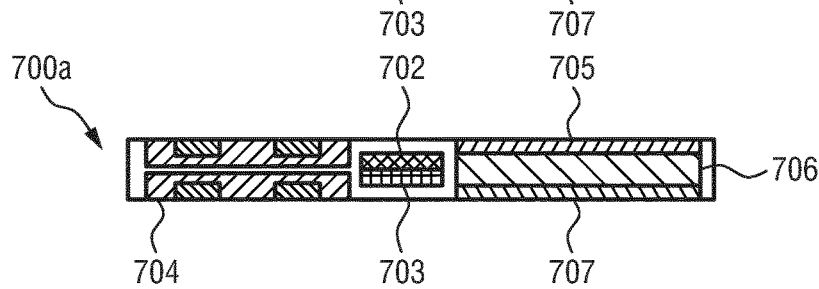
Figure 39A:
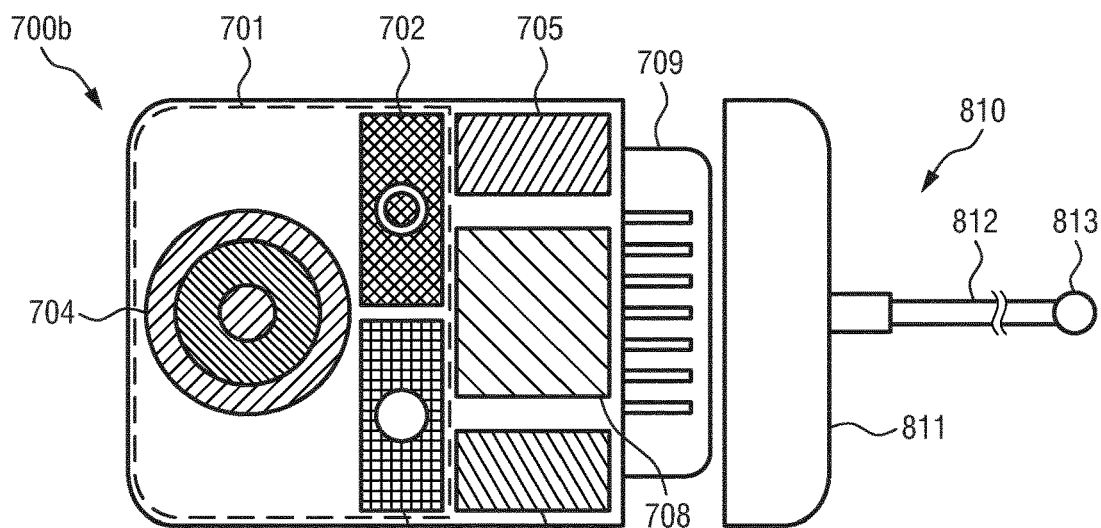
FIGS. 39A and 39B show different views of a second embodiment of a device according to the present invention.
Figure 39B:
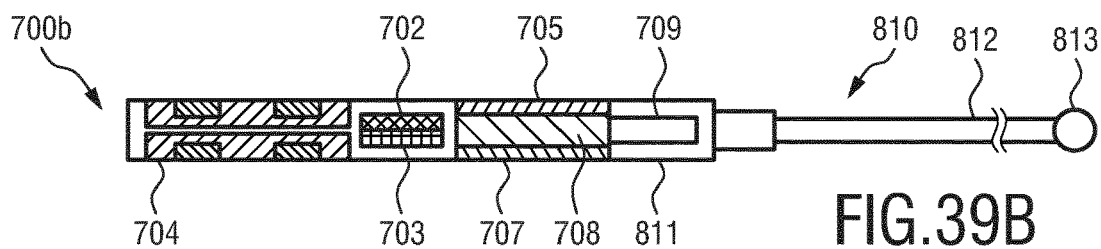
Figure 40A:
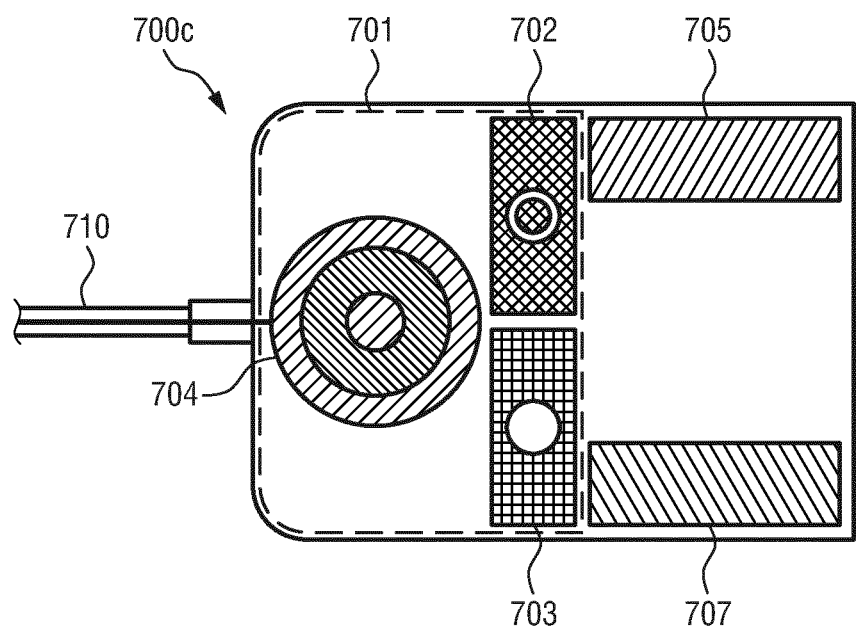
FIGS. 40A and 40B show different views of a third embodiment of a device according to the present invention.
Figure 40B:
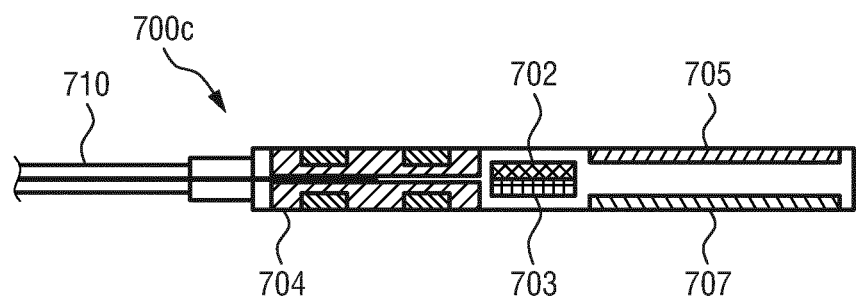

FIGS. 38A and B show different views of a first embodiment of a device according to the present invention, in particular a top view (FIG. 38A) and a side view (FIG. 38B) of a battery module 700a. FIGS. 39A and B show different views of a second embodiment of a device according to the present invention, in particular a top view (FIG. 39A) and a side view (FIG. 39B) of a measurement module 700b. FIGS. 40A and B show different views of a third embodiment of a device according to the present invention, in particular a top view (FIG. 40A) and a side view (FIG. 40B) of a cable module 700c.

The different modules 700a, 700b, 700c shown in FIGS. 38, 39 and 40 each comprise a connector 701. The connector 701 comprises a data transmission unit 703 arranged for transmitting data to and/or receiving data from another device 700a, 700b, 700c of the system having a counterpart connector, and a magnetic coupling unit 702, 704 for transmitting power to and/or receiving power from another device 700a, 700b, 700c of the system having a counterpart connector by use of inductive coupling using a high frequency power signal. A detection unit 705 is provided for detecting coupling of a counterpart connector of another device of the system with the connector 701. A control unit 707 uses the detection that a counterpart connector of another device of the system has been coupled with the connector 701 as a trigger to determine and/or reset a relative time difference between a clock signal used by the device and a clock signal of the other device using the high frequency power signal of the magnetic coupling unit 702, 704 and a magnetic coupling unit of the counterpart connector and/or using a received time calibration signal for determining and/or resetting the relative time difference.

In an implementation the modules 700a, 700b, 700c each comprise a coil 704 (for inductive power transfer), a rectification section and converters for stable voltage(s) and power generation and at least one radio (BT4, BLE, Wi-Fi, ZigBee, etc.). The battery 706 of the battery module 700a can be charged and discharged in a contactless manner. An embodiment with devices coupled when they are in close proximity will be described first.

When a battery module 700a is connected wireless to a patient monitor (by radio or NFC or by module detection), a patient ID and time stamp of the monitor are assigned to the battery module 700a. Next a measurement module 700b (e.g. for ECG) is added to the battery module 700a such that the coils 704 in the modules 700a, 700b are aligned and are in close proximity (the alignment accuracy depends on the type of coil use, for an air coil the requirements are relaxed (e.g. in the range of mm to cm), for a coil with a high magnetic permeability alignment is in the sub mm range). Now power can be transferred between the modules 700a, 700b and the presence of the second module is detected by the first module.

This detection can be either by a magnetic, electric or optical means. The time of detection of module can be used as a time stamp and can be stored in a master device of the wireless system (in this example the battery module 700a). For the power transfer an AC signal with frequency in the order of 100 kHz may be used. Since this power signal is identical for module 700a and 700b it can serve as a relative time measurement by for instance using a simple counter. Drifts in this frequency are of importance for absolute time but not for the relative time which is within one cycle the same for the modules (<10 μs error).

Adding a second measurement module can be done in a similar method as for the first measurement module, e.g. by stacking this module on top of the battery module or the first measurement module 700b. The same stacking detection mechanism can be employed for detection of the second measurement module and this can serve as a third time stamp for second measurement module. Again this time stamp number 3 can be stored in the master device (here the battery module 700a).

Data is sent wirelessly from the measurement module(s) to the battery module and via the battery module to the monitor (can also be directly to monitor). The data blocks contain information of the type of measurement, channel information, information on measurement settings (signal processing delays), the time stamp and (relative time) counter value of the first measurement byte. Data can be submitted for instance in four blocks each containing 20 bytes consisting partly of ID and information and measurement data and parameters (like heart rate, SpO2 value, etc.). Data is received in the monitor where it is further processed, more complex parameters may be extracted and waveforms and parameters may be plotted on the display.

As shown in FIGS. 39A and B, the measurement module 700b further comprises a galvanic connection unit 709 for galvanic coupling of the measurement module 700b to a third device 810, e.g. a sensor, having a counterpart galvanic connection unit 811. Further, a patient side connection unit 708 may be provided for connecting the device to one or more sensors 810 to receive one or more physiologic sensor signals. The sensor 810 may e.g. be an ECG sensor comprising a sensor element 813 (e.g. ECG electrode) connected to the counterpart galvanic connection unit 811 (also called sensor connector) via a lead wire 812.

The cable module 700c further comprises a cable 710, which may be provided at its other end (not shown) with another connector (like the connector 701) for coupling the cable module 700c with other modules or with a monitor.

In another preferred embodiment one battery module powers at least two stacks of measurement modules in different locations on the body. Again, one common power signal dictates the timing pace, while stacking detection or radio-messages are used to one-time trigger (re)set of the relative time difference. FIG. 41 shows a schematic diagram of a first embodiment of a system including different devices according to the present invention. In this embodiment there is only one battery module 700a in the system. The second measurement module 700b2 of two measurement modules 700b 1, 700b2 (each connected to a respective sensor 810a, 810b) is powered by a data/power cable module 700c (having a connector 701 at each end) that is connected to the combination of battery module 700a and measurement module 700b2.

Battery module 700a and the first measurement module 700b2 are paired to the monitor and each other in the same way as described above with reference to FIGS. 38 to 40. The second measurement module 700b 1 is connected to the battery module 700a via a shielded cable module 700c that can have a two way transfer of a radio signal and power. The detection of the cable module 700c at site 1 and site 2 can be done in the same way as described above giving the time stamp 2. The radio in the master can be used to send a message to the two devices for absolute time calibration (this could also replace the time stamp obtained from the stacking detection). Again the power signal is identical for both measurement modules and the battery module so that an accurate relative time of measurement data is obtained.

In another preferred embodiment at least two battery modules 700a 1, 700a2 are connected to least two stacks of measurement modules 700b 1, 700b2 in different locations on the body, connected by the cable module 700c. Such an embodiment is illustrated in FIG. 42 that shows a schematic diagram of a second embodiment of a system including different devices according to the present invention.

There are two options: Only one battery module is enabled to power all stacks of measurement modules and dictates the timing pace, or each stack is powered by its own battery module and the cable module distributes the power signal (not the power) from one stack to another to dictate the timing pace.

This embodiment differs from the embodiment shown in FIG. 41 since there is more than one battery module in the system. This complicates the system as there are now two different power signals which differ in phase and frequency. Both can change in a different way due to temperature changes etc. The cable can be applied to both devices, giving a new common time stamp. One of the two battery modules 700a1, 700a2 is switched off (i.e. could be the one with the largest remaining energy), hence there is only one battery module active in the system. Relative time measurement is then similar to the above two embodiments. When the battery energy is below a predetermined level (i.e. 30%) this battery module can be switched off and the other battery module takes over. This is a new time stamp, now the power clock signal of the second battery module is used for relative time.

FIG. 43 shows a schematic diagram of a third embodiment of a system including different devices according to the present invention. In this embodiment there are multiple nodes, each powered by a separate battery module 700a1, 700a2. For practical reasons the continuous use of a cable between modules as in the embodiment shown in FIG. 42 is not possible (i.e. mobile patient). The cable can be used for a short time to generate a time stamp. The battery modules 700a1, 700a2 each will have a slightly different and variable frequency so the tight relative time requirements cannot be met.

A possible method would be to use a master clock signal (could be radio, optical sound) so that each module determines its time from this master clock. This would require additional hardware which would drive cost up. Another method would be to use one of the radios as a master and let the master emit a common short message to the slaves to generate a time stamp. The time of a message received in each module will have an identical delay and this time can serve as a time stamp. Since typical power clock stability is around 100 ppm and assuming that the 100 ppm drift can occur in a period of seconds this time stamp would be repeated every second for an error of less than 0.1 ms. This would require frequent radio contact which could degrade data rates and increases power consumption. A preferred method is described below.

The highest time synchronization is needed for signals that are related to a heartbeat (ECG, IBP, SpO2). The heart rate is a patient specific parameter that can be used as an independent clock to calibrate the internal clocks of each measurement to the one master clock in the system. Note that the heart rate is variable and specific for a certain time interval (e.g. a few minutes). The physiologic signal and its variation can be used for accurate clock calibration by for instance comparing average heartrate over periods of minutes or by comparing beat-by-beat patterns (auto-correlation).

In another embodiment a bedside container module with several measurement modules and one cable to the monitor is provided. This is one module that contains several measurement modules. The power clock is identical for each measurement module. At insertion of a measurement it is detected automatically and a time stamp is generated at the detection time. Since the module is connected to the monitor via a cable, the system time from the monitor device can be used for absolute time.

In another embodiment the heart rate may be used as common clock to dictate pace. Virtually all measurements (SpO2, ECG, NIBP, invasive temperature, etc.) also determine the local heartbeat of the patient, which can be used as a global clock signal to dictate the pace of the relative timing between measurements. Timing noise can be smoothened by local PLL or FLL functionality e.g. inside each measurement.

Still another embodiment uses local correction. In this embodiment every module has its own crystal clock for determining the timing. By first connecting modules (as described in previous embodiments) deviations of each crystal with respect to the distributed master clock can be calculated. Next, modules are disconnected and said deviation is used to correct the timing accordingly. This assumes that temperature drift of crystal clocks is equal for all of them and drift rate variation is small.

According to another embodiment synchronization is achieved by occasionally sampling power pulse counters. In this embodiment each module simply continuously counts the number of power pulses on (each of its) input/output power transformers. Each counter resets to zero when the module powers up and/or when its corresponding power signal is interrupted and/or on another externally generated synchronization event. This mechanism ensures that the counter values on both sides of the transformer formed by two stacked modules are always identical, even though in some of the cases the two counters in a single module may have different values (to be discussed in the next embodiment). The module now occasionally registers a counter value together with its internal time stamp. This information is very similar to a synchronization exchange between two units with a packetized data link. The counters do not need to have a very large range. A synchronization algorithm like described in Section 4.3 of Plomp et al., "Considerations for Synchronization in Body Area Networks for Human Activity Monitoring, Int J Wireless Info Networks 18 (2011): 280-294 can be implemented with very low resources—either in the module itself, or in a central receiving unit that collects the information—and is sufficient to reconstruct accurately the phase and frequency relation between the power signal and the module's internal clock.

In another embodiment local synchronizations are linked in a chain. In this embodiment there is no requirement of a single power beat signal coming from a single power source that passes through multiple modules. Each module can decide to pass the incoming power signal to a next neighbor, or block it (because the neighbor is already powered and trying to supply the module from the other side), or regenerate a new power signal with different frequency and phase. Assuming that the system knows which module/side shares a direct power connection with what neighbor module/side, the relative phase and frequency relation between all neighboring module clocks can be reconstructed in the following manner:

1. Reconstruct the phase and frequency relationships between a module's internal clock and the power signals on both sides, e.g. in the manner described in the previous embodiment.
2. Power signals on both sides of a transformer formed by two stacked modules are always identical, the relative phase and frequency relationship between neighboring modules can now also be established.

Figure 44A:
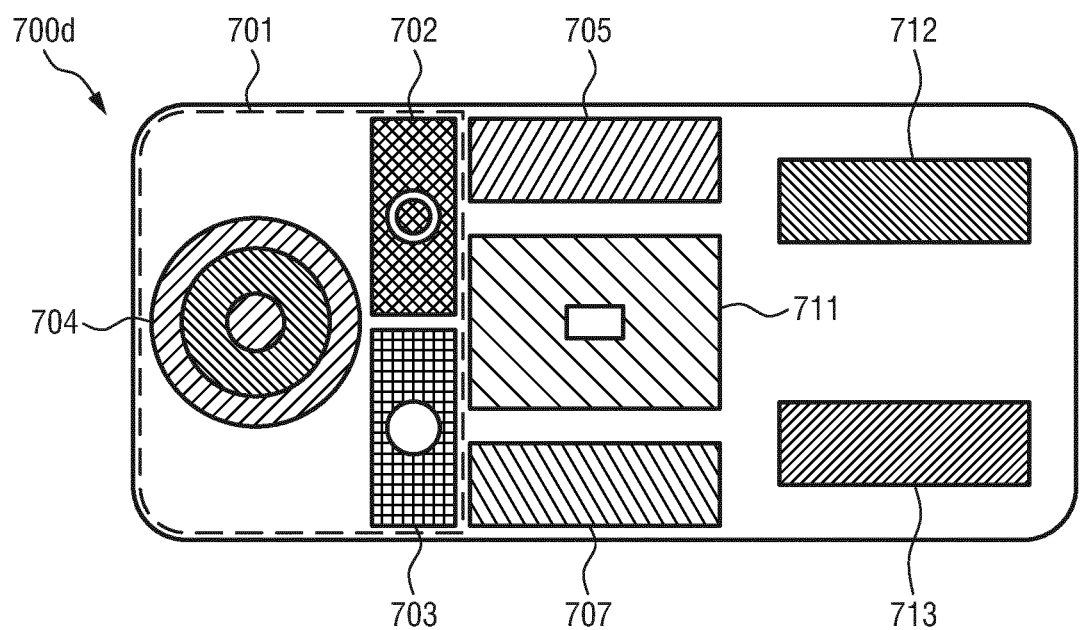
FIGS. 44A and 44B show different views of a fourth embodiment of a device according to the present invention.
Figure 44B:
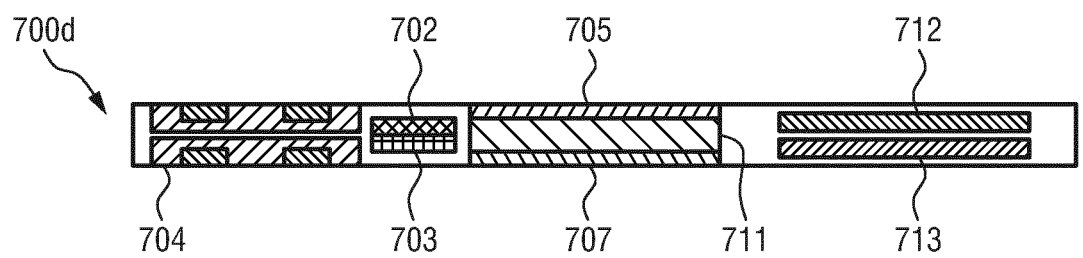

FIGS. 44A and B show different views of a fourth embodiment of a device according to the present invention, in particular a top view (FIG. 44A) and a side view (FIG. 44B) of a module 700*d*. The module comprises a storage unit 711 for storing the moment of detection that a counterpart connector of another device of the system has been coupled with the connector 702 as a time stamp. The data transmission unit 703 may then transmit the time stamp and/or a determined relative difference between the clock signal used by the device and the clock signal of the other device to the other device for storage in a master device of the system.

Further, in this embodiment the module 700*d* further comprises a clock unit 712 for generating the clock signal used by the module. Further, a counter 713 may be provided for counting the number of pulses of the high frequency power signal, wherein the counted number is used for calibrating the clock signal used by the module. The counter may reset to zero when the device is coupled to or decoupled from another device or when the inductive coupling is interrupted or when an external synchronization event is detected.

Figure 45:
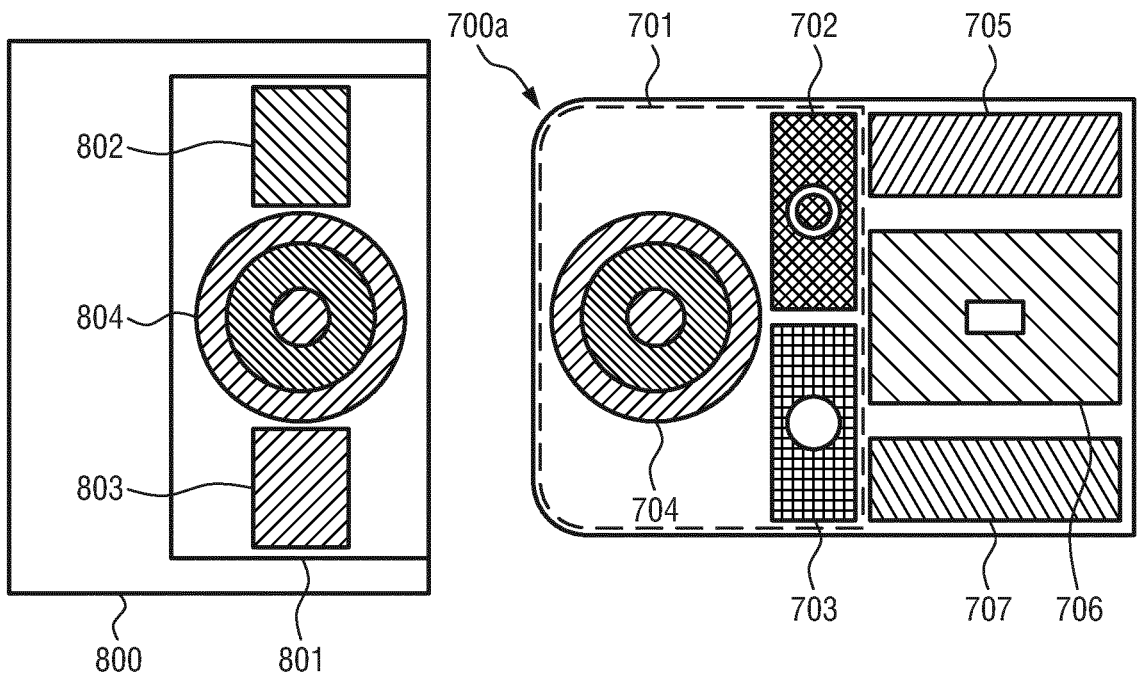
FIG. 45 shows a schematic diagram of a fourth embodiment of a system including different devices according to the present invention.

FIG. 45 shows a schematic diagram of another embodiment of a system including different devices according to the present invention. In particular, a battery module 700*a* and a monitor 800 are shown which may be coupled wirelessly. The monitor 800 comprises a connector compatible with the connector 701, including a data transmission unit 803 and a magnetic coupling unit 802, 804.

Figure 46:
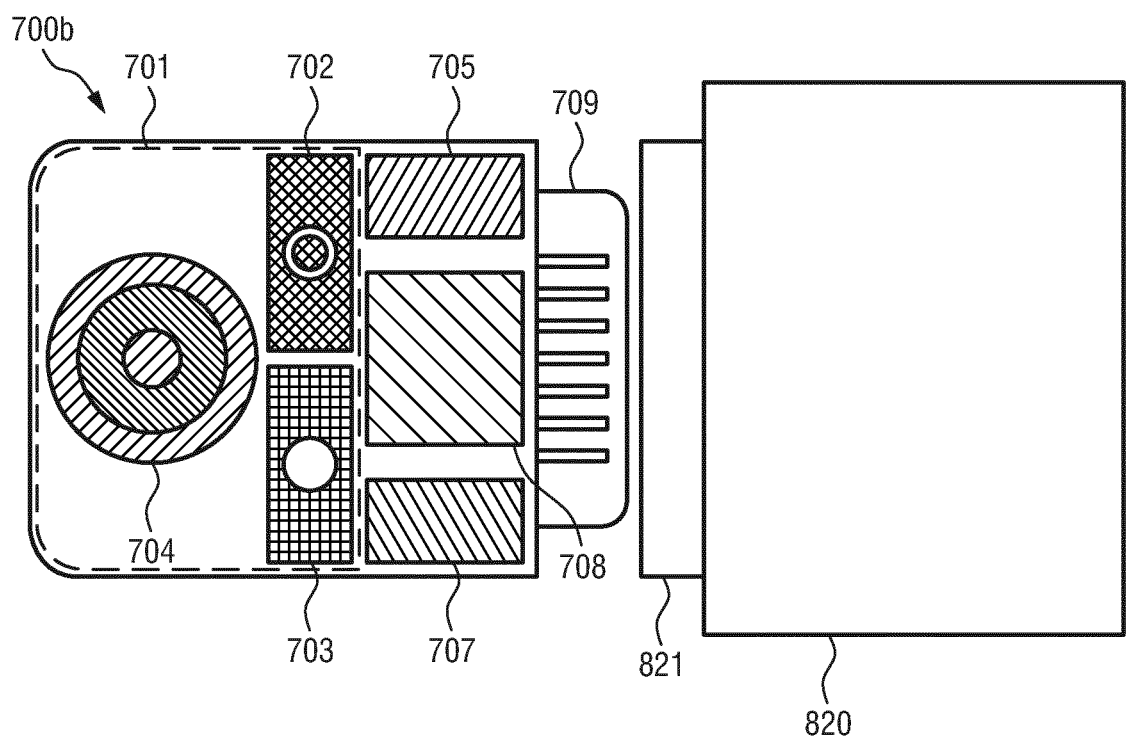
FIG. 46 shows a schematic diagram of a fifth embodiment of a system including different devices according to the present invention.

FIG. 46 shows a schematic diagram of still another embodiment of a system including different devices according to the present invention. In particular, a measurement module 700*b* and a third device 820 including a counterpart galvanic connection unit 821 are provided that are galvanically coupled, for instance to receive a master clock signal from the third device 820 for calibrating the clock signal used by the measurement module 700*b*.

One main advantage of the present invention is that a universal approach is provided that may generally serve all patient monitoring applications, which is a key factor to achieve in efforts to reduce costs. Further advantages are the modularity and the direct compliance to existing connectivity standards for wireless measurements.

The application of the present invention is not limited to patient monitoring, but can be extended to mutually isolate modules (sensors, actuators) connected to a common entity in e.g. automotive or cattle breeding (central milking machines connected to multi-cows). Further, the present invention is not limited to the explicitly disclosed types, forms and numbers of antennas or coils, which are to be understood as examples only. Components used in the disclosed embodiments may also be configured as being compliant with the Qi standard or other wireless power standards, and also standard components compliant with the Qi standard may be used for single components according to the present invention, if possible from a technical point of view. Further, a device may comprise means for vertical and horizontal stacking and include corresponding coupling means for coupling in the respective direction, i.e. a device may e.g. comprises a combination of the connectors as shown in FIGS. 25A and 26A.

The present invention can be applied for dielectric isolated wearable vital sign wireless sensor devices where time synchronization between signals needs to meet tight limits. Potential applications are in patient monitoring, low acuity monitoring, wearables, continuous blood pressure, etc.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. Device for wireless transmission of at least one of data and power between the device and another device of a system, comprising a patient monitoring system, said device comprising:
   a connector comprising a data transmission unit arranged for at least one of transmitting data to and receiving data from another device of the system having a counterpart connector, and a magnetic coupling unit for transmitting power to and receiving power from another device of the system having a counterpart connector by use of inductive coupling using a high frequency power signal,
   a detection unit for detecting coupling of a counterpart connector of another device of the system with the connector, and
   a control unit for using the detection that a counterpart connector of another device of the system has been coupled with the connector as a trigger to at least one of determine and reset a relative time difference between a clock signal used by the device and a clock signal of the other device using at least one of i) the high frequency power signal of the magnetic coupling unit and of a magnetic coupling unit of the counterpart connector and ii) a received time calibration signal for determining and/or resetting the relative time difference, and
   a data storage unit for storing the moment of detection that a counterpart connector of another device of the system has been coupled with the connector as a time stamp.

2. Device as claimed in claim 1,
   wherein the detection unit is configured to detect coupling of a counterpart connector in a magnetic, electric or optical manner.

3. Device as claimed in claim 1,
   wherein the detection unit is configured to detect coupling of a counterpart connector by at least one of (i) detecting if the strength of magnetic coupling between the magnetic coupling unit and a magnetic coupling unit of the counterpart connector exceeds a magnetic coupling threshold, in particular by detecting impedance, resonance frequency or induced voltage, and (ii) detecting if the intensity of data received by the data transmission unit from a data transmission unit of the other device exceeds an intensity threshold, in particular by detecting signal intensity or antenna impedance of an antenna of the data transmission unit.

4. Device as claimed in claim 1,
   wherein the data transmission unit is configured to transmit at least one of the time stamp and a determined relative difference between the clock signal used by the device and the clock signal of the other device to the other device for storage in a master device of the system.

5. Device as claimed in claim 1,
   wherein the other device comprises a battery and wherein the high frequency power signal used for transmitting power from the battery to the device is used for at least one of determining and resetting the relative time difference.

6. Device as claimed in claim 5,
   further comprising a battery, wherein the control unit is configured to switch off the battery or generate a control signal for transmission to the other device for switching off the battery of the other device.

7. Device as claimed in claim 1,
   wherein the data transmission unit is configured to receive a master clock signal from the other device or to transmit a master clock signal to the other device.

8. Device as claimed in claim 1,
   further comprising a galvanic connection unit for galvanic coupling of the device to a third device having a counterpart galvanic connection unit and for receiving a master clock signal from the third device for calibrating the clock signal used by the device.

9. Device as claimed in claim 1,
   further comprising a patient side connection unit for connecting the device to one or more sensors to receive one or more physiologic sensor signals,
   wherein the device is configured to calibrate the clock signal used by the device based on a periodicity of a received physiologic signal.

10. Device as claimed in claim 1,
    further comprising a clock unit for generating the clock signal used by the device.

11. Device as claimed in claim 1,
    further comprising a counter for counting the number of pulses of the high frequency power signal, wherein the counted number is used for calibrating the clock signal used by the device.

12. Device as claimed in claim 11,
    wherein the counter is configured to reset to zero when the device is coupled to or decoupled from another device or when the inductive coupling is interrupted or when an external synchronization event is detected.

13. Device as claimed in claim 1,
    wherein the control unit is configured to decide if a received or generated high frequency power signal is transmitted to the other device or if a new high frequency power signal with different frequency or phase is regenerated.

14. Device as claimed in claim 1,
    wherein said data transmission unit is configured for transmitting data by use of RF transmission, optical transmission, capacitive coupling or near field communication.

* * * * *